United States Patent
Takatsuji (12)

(10) Patent No.: US 7,098,382 B1
(45) Date of Patent: Aug. 29, 2006

(54) PROMOTER HAVING SPECIFIC ACTIVITY TO PISTIL TISSUE AND USE OF THE SAME

(75) Inventor: Hiroshi Takatsuji, Ibaraki (JP)

(73) Assignees: National Institute of Agrobiological Sciences, (JP); Bio-Oriented Technology Research Advancement Institution, (JP)

( * ) Notice: Subject to any disclaimer, the term of this patent is extended or adjusted under 35 U.S.C. 154(b) by 0 days.

(21) Appl. No.: 09/979,433

(22) PCT Filed: May 21, 1999

(86) PCT No.: PCT/JP99/02692

§ 371 (c)(1),
(2), (4) Date: Apr. 17, 2002

(87) PCT Pub. No.: WO00/71704

PCT Pub. Date: Nov. 30, 2000

(51) Int. Cl.
*C12N 15/82* (2006.01)
*C12N 15/29* (2006.01)
*A01H 5/00* (2006.01)

(52) U.S. Cl. .................. 800/287; 800/271; 800/317; 800/323.1; 800/278; 536/24.1

(58) Field of Classification Search ............. 800/323.1, 800/317, 278, 290; 435/320.1, 468, 69.1, 435/320; 536/23.1, 24.1
See application file for complete search history.

(56) References Cited

OTHER PUBLICATIONS

Fricker et. al. (Multiple elements of the S2-RNase promoter from potato are required for cell type-specific expression in transgenic potato and tobacco, 1998, Mol. Gen. Genetics, vol. 257, No. 2, pp. 132-142).*
Goldman, M.H. et. al., EMBO J. vol. 13, pp. 2976-2984, 1994.*
Harikrishna, K et. al., Plant Mol. Biol. vol. 30, pp. 899-911, 1996.*

\* cited by examiner

*Primary Examiner*—David T. Fox
*Assistant Examiner*—Georgia Helmer
(74) *Attorney, Agent, or Firm*—Perkins Coie LLP

(57) ABSTRACT

A novel promoter is provided which has an expression activity specific to any pistil tissue. The promoter has any one of the DNA sequence from position 1 to 2595 of SEQ ID NO. 1, the DNA sequence from position 1 to 2322 of SEQ ID NO. 2, and the DNA sequence from position 1 to 2012 of SEQ ID NO. 3, and a part thereof. A method for producing a plant having a modified trait by introducing a heterogenous gene operatively linked to the promoter into a plant, and a plant having a modified trait produced by the method are further provided.

10 Claims, 18 Drawing Sheets

FIG. 1   ZPT1-10-GE Sequence

```
         10         20         30         40         50         60
1234567890 1234567890 1234567890 1234567890 1234567890 1234567890
GATATCGCTT CACTACCGTC TGTTGGTGGC CCAATGACAT TTAGGGGGTC GGCGAAATTA    60
ACTATTTCAC CACCAATGAT CACGGTGGTG GTGGTGGTGG CGGCAGCAGG AATTTCATCG   120
CCAGAATGGC TGCTAGAGTT CTGAGCAGAA TGGTGGCAG  ACTTCTTCTT TTTTTACAAA   180
GAAGCTTGTG ATTACGACTT TAATTATAGA TTTCAATAAG CACAAATAGG AATTTCTCTT   240
GCTTCGAAAT TGCTACAGTT GGAATAAGAT AAAGTAAAAA TGGTGGTGTG ATTAAGTGGG   300
CATTTATATG TGAGAAGTCA TCATTGTCTT GGGAAGGAGG ACGAAATGGC GCAACCTTTC   360
CAACGGTCGC CGCGTGTAAC GGATGGGAAG GTGAAGCGAT GGCTACCTTT TGAATTACT    420
TGCACACGA  GCAGCCACAC CACTTCTCCC GCTTGTTTTT CATTCCACTC CTCGGCACT    480
CTGGCAATTG CTCGAGGAGT AGGGGACTA  TCTGTACTGG GCAAAATATG ATTGCACAC    540
GTACCCGCCG AAGCATAAAG TTCGGGATAC TTTTGCAAG  ATTCACAAGT TGGATGACGT   600
AGCGACATGG CTTCCGAAGC GAAGCCTCAG GATCGAGATC ATTTGTAAGC GTCGTAATAT   660
GATCGCTTCA GAGAACAGGC AGTTCATCGC CCTAAGGTGA AATGATCTTA ACCTCAGGAG   720
GATAGTTCGG CTACAGCGTA AGAGGCGCCC CATGATCTCC GCCCAGTATC TCAGCATTTA   780
ACGGGTAAGA TTTGGGGCAG ACCACAATTT AGATAGAGTG GGCTAATTAA TGCCCTTAAT   840
TGTCACTAAC ATATGGTCTA TAAGTAAAAT TCATTTTATC TTGTAAAGAT ATTCACAAAT   900
TTATAGGCAA TACTCTGCCC AATTGTAATC TCAAGGCATT CATATTGAAA TGGTTACTTT   960
CTGCTCTTAT TGTCCATTCA TTTCCATTAA TTTCTTGTCC TTTACCAACT TTGATACATC  1020
AAATTATTTG TAAAATATAA ATTCAATTAT TTCCCTACTC CGATTTAGAG AAATATAATT  1080
ACTACTATAG ATTAAAATAC AAATTTACAT TATCAAAATA AATCTAACAA AGTACACATA  1140
AACAAGCTTG TAAAAGTAAG CGTGTGGAAA TGGGATCTA  ACAAAAAGCA TGATGCACGA  1200
CTAGGTCCTT TCTTTTTTCC CCCAACAAGA CGCGATGCAT TTACTTCCCT AGAAAACTCC  1260
TTTTTCAAAC GAATAGGATG AGAACGTTAG TAATTTCCTC CCTAGCAACC CCCACCCATG  1320
ACCCATCATC TTTCATTCCC AATCAGAGAA AAAATTTAGC TCAAGATCCT TAATTAAAGG  1380
ACATTATAAT TTCCAAATTA TTTATTATTC CTTCGCTGTT ATAAGATAT  AATAAAAACG  1440
TATGAAAGTT CAGCCAACGT ATTAAATAAG ATGCCACAAT TTGTGGTCG  GCCCAGCCAG  1500
```

FIG. 1 (continued)

```
CACCATGCCA AAATTTTCAC CTCCTAGCCT TGTAGTGGAA AATTTTATCC ATCCACCACA    1560
TCCTCGACTG AGAATCGACA TCACAAGCAC AAGCAAAGAT TCACTAGTGG AGCTTCCTCC    1620
AGGTAAAGAG GGGGTTACTT TGGTGGTTGG TCATACCCAA TTTAAACACA TGACATACAT    1680
ACATACATAC AGTGGCTTGG TGTAAAAAAA TTTGTGGGT AAGTTTTAG TACAATTTAT      1740
TTGTCTCCGT CCTTAATTCA ATACCAGCAG TTTTGTTGAC TGTTTACGAA ATTAAGTTAA    1800
ACTAAATTTA ATATCCTAAC CTCTTTTCTT TTTTTTCTTT TTTTTATAAT GGTTTAATTA    1860
CAAATTCTTG GCAAGAGTG ATGTAATCTT TAGCAAAGCA TAGAGTATTT TATGTGATCC     1920
TTTTTCATAT AATAAGAGGG AAACGTATTT AAAGGCCCAA GTTAACAGAG GATAGAAAGG    1980
ATTATATCAA GTTTGATCCG ATATACAATC CAGTATTTTA TTTATATAAT CCAGTATAAT   2040
ACGTCAAATT ATACCGTCAT TGTAAAATTA TTGTCAAATA CATTAACTTA AACCCTTTAT   2100
TAAATTACCC CGCATAACAT GTGTAGGGTT ATTTAGGAAA AGTAGAGATG GGATTGAACT   2160
AAATGCAAAG CTCGCATGTT ACATGTTGTT CCCTTCTACT CTCTTTTCTA TCTTTGCCTT   2220
TATGCATACG TTTTAATTGA GTTTTCTTTA TTAATTGCAT ATTTCCGTTT TAAAGAAAAT   2280
TACTTCCAAT TAATTCAGAA TCTAACTTTC TCTTAAATGT TTTTTTTTC TGTTGTAAAA   2340
ATGTCATCCC TTAAATATTC TTGCTCTTTA TATTCTTGGT GCAGGAAGAG TGCTCGTCAC   2400
ATACTTTAAA ACAATTCAGA GTATTTGCAA GAACAAAACA CGGACAACAC ACAGCAAATT    2460
AGTGAAGAAA CAGACTCAAT TCCCTCAATT TCATCATCCC CAGAAGATGA AGAGAATGCG   2520
AAGAAAAAGA TATTGAATTA TAGGATCAGA GTGAATCCAA AGAAGAGCCT TAGAATTATG   2580
                                                              M
GATCTTCTAC AAGATAGAGA GAGTGAAACC GAGTCATTAC CATATCCAAC ACAATGTAAA   2640
 D  L  L  Q  D  R  E  S  E  T  E  S  L  P  Y  P  T  Q  C  K
CGATACAAGC GGATCATAAA CTCAAGAATC TCAGATACAC ATTACAATCA GTTTTTATCA   2700
 R  Y  K  R  I  I  N  S  R  I  S  D  T  H  Y  N  Q  F  L  S
TTAGAACGAC GACGACAACA ACAACAACAA CAGTATGGAA AGATTACAGA GTTTCCATTT   2760
 L  E  R  R  Q  Q  Q  Q  Q  Q  Y  G  K  I  T  E  F  P  F
GTTGAGTCTG AGCCAGTGAG TTCAATTTCA GACACTTCAC CAGATGAAGA CGTTGCGAAC   2820
 V  E  S  E  P  V  S  S  I  S  D  T  S  P  D  E  D  V  A  N
TGCTTGATGA TGTTATCTAG AGATAAGTGG ATGACACAAG AAAATGAAGT TATCGACAAT   2880
 C  L  M  M  L  S  R  D  K  W  M  T  Q  E  N  E  V  I  D  N
AGTGCTAGCT ATGATGAAGA TGTAAAAACA GAGGACTCTG TAGTTGTTAA AGTGACAACG   2940
 S  A  S  Y  D  E  D  V  K  T  E  D  S  V  V  V  K  V  T  T
ACTAGGAGGG GTAGAGGTAA GTACATATGT GAAACATGTA ACAAAGTTTT TAGATCTTAT   3000
 T  R  R  G  R  G  K  Y  I  C  E  T  C  N  K  V  F  R  S  Y
```

FIG. 1 (continued)

```
CAAGCACTTG GTGGTCATAG AGCAAGTCAC AAGAAGATTA AAGTCTCAAT TAATGAAACA   3060
 Q  A  L  G   G  H  R    A  S  H    K  K  I  K    V  S  I    N  E  T
AAAAACAATG GAAATGTAGA AAGTGAGGTT CAAAAGGATA AAATACATGA ATGTCCTGTT   3120
 K  N  N   G  N  V  E    S  E  V    Q  K  D  K    I  H  E    C  P  V
TGTTACAGAG TATTTTCATC AGGACAAGCT CTTGGTGGAC ACAAGAGGTC ACATGGTATT   3180
 C  Y  R  V   F  S  S    G  Q  A    L  G  G     H  K  R  S    H  G  I
GGTGTAGCAG CCACAAATGT GAGTCTTTCA ACAAAAATTG TATCATCAAG AATTAGTGGA   3240
 G  V  A  A    T  N  V    S  L  S    T  K  I  V    S  S  R    I  S  G
ACTATGATAG ATCTCAATAT TCCTGCTACA TTGGAGGATG ATGAGATTAG TCAAATTGAG   3300
 T  M  I  D    L  N  I    P  A  T    L  E  D  D    E  I  S    Q  I  E
GTTTCTGCAG TTTCTGATGA TGAATTTGTC AACCCCTGAG TCGAAGGTCT ATCAGAAAGA   3360
 V  S  A  V    S  D  D    E  F  V    N  P
ACCCCTGTAG GAGTAAGATC TGCGTACATC TCACCCTCCT CAGAATTCAT CTGTAGGATT   3420
ATATCAGGTA CATTGTTATT GCTGTTGAAT TTGTCATCCC CATCAAGCAC TGAAATGATG   3480
TTATTCTTAG AGTTAATGAA ACTCAAGAAT TATAGGTAAA GTTTGTTCT TATTTTGACC    3540
TTTTTAAGTT CTTAGGTATG GAACTAAGGA AATTGATCAG TACTTTTCT TGGAAAACAT    3600
TAGCACTTTC CAAGCTATAC TCATTGAATA TCTGAATAGT TTTGACTGTA ATTAAATTTT   3660
CCAACTCTGC TTTGTTTATG TTACAGCTTA TTAATATCAT CTATTAATTT AACTCTGTTC   3720
TGT                                                                 3723
```

FIG. 2  ZPT3-3-GE Sequence

```
         10         20         30         40         50         60
1234567890 1234567890 1234567890 1234567890 1234567890 1234567890
CGAATTGGGT ACGTCGACGT ACATCCATT  ATCTTTCCT  TCTCTTAGTC CTTGTATTGG    60
AATAACTTCT TCCATTTTTT AATTCCAATA AACTTGTCCC TTCAAATTAT ATGTTTTACT   120
TTTTTAAAAT TTAGATAGTT AGTAGGAAAT GAAGACTGCA ACTATCAAAT AATGGAGTAT   180
GATGGATGAG ACCCCTCCAC TATTTATGTA CCGCAACTCG AAATTAATCT GTTCAGTAAA   240
TATCGAATAC AATATGGTTA TAGAAAAACA AAATACATAA AGTAAGAAAA TAAAGGGACA   300
GACAAGAACT TTCCCTTTG  CATCGAATAG AAAAAGGAAG ATAAAAATGG ACTAACAAAT   360
TAATTACAGT TGAAACTATA AGTACGAGTA AATTTCATTG ACGGTCACCC AACTTTCATG   420
TTTGTTATCC AAAAGTTACT ATTATTTCAT ATGTTATCCA AAAATCATTT AACTTTATTT   480
TAAGTTACAT AAAAATAATT TTGCCATGAA ATAGCTTAAT ACATGCTTGA AAATGACTTC   540
ACTAGAGTAC ATAATTTTGA TTAAATATAA TTAATGTATT AAACTCCTTA CTTGACCCAT   600
ATTAAAAATC TGACTCAGTT GTCTAAAGCT CATACAAATC TTACACACTC AAATTATTGG   660
GTTAGCTTT  CTATTTTGTT CTTTTTATTG TTAAGTTTTA CTGTTTAAGT TATTGGTATA   720
GTTATTTTGT ATTTCTTTTT TGTGCTATCC GGCGCAGTAA CAATAAATTA TCAAATAGAA   780
GGTTGCAACC AAAACAACTT CTAATTTTAA CTTTTCATAA TAGTGGATTC GAGAGGAATC   840
CATGATTTTC TTGGAAAATA ATTTTTTAGC ACATAATAGC CCTAGCAGAG AGAACCAAGA   900
GAGAAATTTG GAAATAAGCA AATACTGATA TATGAATTAG TGATTTAAATC TTAATTTAAT   960
TAAGCAATCT TTTATTTTAA CTTCCACGTC ACTTTTCAGG CGTGTATTAA TAAGTTAGTT  1020
CCGGACAAAA TTATTTTTGT GCAACTTAGG TAAAAATTGA ATGATTTTTG GGTTACAAAA  1080
AAAAAAAAAA AAAAAAGAAT AGTGATCTTT AGTTAACAAA TATGAAAATT GAATGACCAT  1140
CCATGAAATT TACTCTTACC CATGAAATTT ACTCCTATAA GTACTAACAA GAACTTTTCT  1200
TATTTGTCTG TTGTTAGATT AATCGGTAGA GCTTCCTATA CAATAGTTCA AACCAAAATA  1260
TCTGATCCGT CGTTACAACC ACCAAGCAGT TTCCTTGACT CAAATTAAGT AAAGGTTAAA  1320
CCTAATTATT TCTAGGAAAC TCTTTTCTTG TCTCCATTTG CCCGTCTTGT CCATTAATAA  1380
GAAAAACAAA TGAATTTAAG TTTTATCCAC TAATAGTAAA AAGAAAATTC TACATTACCA  1440
ATGTTATATT TTGGACAAAT TCTACTAATA GGTTACTGAT CCTCTTATTA GGATTATCAA  1500
```

FIG.2 (continued)

```
CTTATAGTCA CCTAAATGCA GCTAGTTTTA AACGATTTCG TTGTGTAAAT AATTTTTAAA   1560
ATACCTCAAA ATTAAATCTA TTTTTCTTGA AATCAAATAA TTTAAAGAGG AAATCTCAAT   1620
TGGTAATGCT TTCTTTAGTA AGTTAATTGT TGTAAATATT CATGTGGGAT ATATGAAGTC   1680
AACTCTACTT ATATTTTAGG TAACGTAATA ATTTAAAAAA TTTAATTAAA TAGTAAGTCC   1740
CTCGTCTCAC TTTATTTATC ATACATTTTT TAGTCCATCC AAAAAAGAAT ATCATTTTAC   1800
CATTAATGAA ATGATTTATA TTCACACAGA TACCTATTGT TTGTTTTAGA TCATAAATTT   1860
TAAAACACTT TTTTTATTTA TTAAATTTTG TGTCAAGTCA AAACATGAAC GAATACAGTA   1920
TTTAAAAGTT AAACTCAAGC AAAAAGAAAA AGAGATTTGT AAAGGGCTGT TTAGAGAATA   1980
TACAGAAGAG ATGGAAATAA ATGCAAAGGT CGCATGTTAC ATGTCCTTCC CATTCACTCA   2040
CTCTGCCTTC ATGCATACGC TTTAATTGAG CTTTTTCTTT TCCTATTAA TTACCTTTTG    2100
CCGTTTTAAG TAAAATTACT CCTACTGAAT CCAAAGTACA TCTGATTTAA CAAATACTAA   2160
TAAATCAGAT TTGTCTTAAA TATATTTCTA TTTGTATATA TCTGTTGGTG GTGGAATGCT   2220
TGTTACCTAC TCCTTTATTC CACTCTCTAC ATAACATAAG AACTCCCAAG AAAACAAAAA   2280
CACACATACT GAGTGTGAAA AATGGAGAAA CACAAGTCAT GTAAGCTATG TTTTAGGAAG   2340
                     M  E  K     H  K  S  C  K  L  C  F  R  K
TTTGCTAATG GTAGAGCTTT AGGTGGGCAT ATGAGATCTC ACATGATGAA TCTTTATGTA   2400
 F  A  N  G  R  A  L  G  G  H  M  R  S  H  M  M  N  L  Y  V
CAAAAACAAC AAATGACTGA TGAAATGGAG TATTCAATTC CTTCATCTTC ATGGTCCTCT   2460
 Q  K  Q  Q  M  T  D  E  M  E  Y  S  I  P  S  S  S  W  S  S
GGTGAAGTAG CTGCTGGTGA TGCCGATGAT TCGGGTATTG TTCTTCCAGA TAAGGAAAGT   2520
 G  E  V  A  A  G  D  A  D  D  S  G  I  V  L  P  D  K  E  S
GAAACTGAGT CATCAAGAAA CCAAGCTCCT TTTAGAAAGT CCAAAAGGTC AAGAAAATCA   2580
 E  T  E  S  S  R  N  Q  A  P  F  R  K  S  K  R  S  R  K  S
AGAATTGTCA AAGTTAAAGA GTACTCATCA TTGGTTGATA CAGAGCCAGT AAGTTCAATA   2640
 R  I  V  K  V  K  E  Y  S  S  L  V  D  T  E  P  V  S  S  I
TCAGAGAATT C                                                       2651
 S  E  N
```

FIG. 3  ZPT2-11 genomic Sequence

```
         10         20         30         40         50         60
1234567890 1234567890 1234567890 1234567890 1234567890 1234567890
GATATCGAGC TAGCCCGGCC CGATTGACAG GTATAACCTA GAGTGTTTCA AATATGACTC      60
GGGATTGGAG AAAGTAGTCA GTTATCTGTT AATCTTTTTT TAAGAGTTGA AGGTGGGATG     120
TCAATTTTCT TAAACTAAAT GTAGTGAAAA CATATTAGTT ACTTCATTTT ACTTACTAAT     180
GTAATGATTA CTCCCTTCGG TCCACTTTAT TTGATTTTTT AATCTTTTTT TTTGTCCAA      240
AATAATTGAT TTGTTCAAAA TTCAAAAAGT TATTAAAGGG TTCTTCCCAA ATATACTCTT     300
ATTAATAAAT AATCTAACAC AATATTTAAA AGACCTCACA GATTTCTACA AATAAATTTG     360
ATAGGAACAA AAGTTAATAT CGTAAATAAT CTCCTTAATT AATGTTAAAA GGTGAATTTG     420
TAAATATGTG TGAAAACAAC AAAAAAAAAT CAAGAGTAAC TATTTGATCC CAAGAATATC     480
AGTACTTATT AGGATAAAGA AAGTAAAATA ATGTGGAAAT GAAATGAACG CTACGTATAA     540
CACGTTGTAA AGGGAACATG TCATTATTCC ATACTTTTAC CAAACCTAAT GATTGGATGA     600
AACATAAGAT TGTAATGGCA GAAATATAAA TTAGGAGAAT TTCAGAAAG CCGGCGTGAT      660
TTTTGGGTCG TAATCAATTA ACTAAGTAAA GTGATGAACC TTGGTTTTAG TAGTAGCACA    720
AAAGTGGGTA GTGGGTCAAC TGCACATGGA ATTTGCTTCA TTCATTAACA TCACTAACTC    780
CAATCCAACC AAGTCCACTC CCACTAGTTA TGCTCAACAA ATATATTTCC ACACTCCATT    840
ATCACTCCAA CTAATTTTTT GTTTCTCCAA AAATAACAAA CGATTTCTCT TCTAATGCAT    900
AGCTAGCATC ATTGTAATTA GATATATCTA AAGAAAATTT ACATGACAAA CTTGTGATCT    960
TATCAGCAAT TAAGATTTAA GTCTCATCAA GCTCTTTCAT TTTCCTTTTT ACTACTTCTA   1020
CCGCTGCTAC TCCAAATGAA AAAAACTTGC ATAAACACTT TGATAGGTA AGCAAATCGC    1080
ACCTATGAAC TTTTTTAAAA TAATTTAATG GTGTTGTTCG AGCTACTATT TGTACACAT    1140
CTAAATTATT TTATATGTAC TATCTCACAG GTATTGAATA ATTTGTCCA CCAAAATTTA    1200
TCGGTATATT GAAAGAAATC ATCTAATGAA TTTTACCTTA ATTTGTTTGG ATCATTTCAC   1260
TTCATTCAGT GTTAGGCGAC GTCCTTTTAG GCTATAGAAT TATACTTATG GACTTGGCAA   1320
TTAAATTTAG TCATTCTTAA TGACAACTGA AGCTAAGGTA GTTAATTAGT ATTTGATGAT   1380
ATATTTAAAA AATGCTTCAA ACTGTGAAGT AACTTAAAGG GTGTGAAATT AAAGAGAGAT   1440
TTATTTTTCT TCTGTATTTT TTAATTGAAG CCGCAAATTG TGTGGTGCCA GGCTTGCACT   1500
```

FIG. 3 (continued)

```
CCAATCCTCC ACAAGGTATC GTTGGCATAA AGTAATGGGG TTTGCTTCAA AGCCAACCGA  1560
ATCTTACTCC TTTCCTCACC TCCTCATACT TCTCATTACT CATTACATTG CATCTTCCCC  1620
CCCCCCCCCC CCCCCCCACG TCCCCAAACC ATAACCTCTA TATACATATA CATATAATCA  1680
CCTTATATAT ATAACTATAT ATATCATTGC CTATATATAT AACTTGCAAA GTTTGTAAGT  1740
GCAAGAAAAC AGTGAACATT TTCAAGATCA CTATTCACGG GGGCGGCTTC TTTTTCACTT  1800
TACCTAAAAT CTCCCTTTCA TTCACTACCA CTCTTCCAAA ACACATATAT ACACTCACTG  1860
TGTTACATCG TTTTCTCCAT TCCCTTTGTG AAATAAAACA TACCTTTGCC TCTTCTTTTT  1920
GTTTCTTTTT CCCCACCTCT TGAAAAAGGT CAGTGACCTT TGAATTATAA AAAAAGACAA  1980
                                       ↑
AGGCACTACA ATGGAAGTTC AAATGCAAGA AGATCATGAT CATCACATGA ATATGGTGAT  2040
            M  E  V   Q  M  Q  E   D  H  D   H  H  M  N   M  V  I
CAAAAGAAGG AGAACTAAAA GACCAAGACC ATCTTCTCCT CTAGCTTTAA CAATTGCTAC  2100
 K  R  R   R  T  K  R   P  R  P   S  S  P   L  A  L  T   I  A  T
TAGCTCATGT AGCACCGTGG AAGGGACTCA TGCTGGTGAA TTGGACGGAC ATGTGGCGAA  2160
 S  S  C   S  T  V  E   G  T  H   A  G  E   L  D  G  H   V  A  N
TTCGTCGTCT TCGCCTTCAA ATTCTGGGAT TGATATACTT ATCAGAAATA GAGAAGAAGA  2220
 S  S  S   S  P  S  N   S  G  I   D  I  L   I  R  N  R   E  E  E
AGATATGGCT AATTGTTTGA TTCTTTTAGC ACAAGGTCAT AATAACCAAA AGCCGTCTCC  2280
 D  M  A   N  C  L  I   L  L  A   Q  G  H   N  N  Q  K   P  S  P
TTCTCATTCT CCATTGGATG TCTACCAATG CAAAACATGC AACCGTTGTT TCCCTTCGTT  2340
 S  H  S   P  L  D  V   Y  Q  C   K  T  C   N  R  C  F   P  S  F
TCAAGCACTT GGTGGACATA GAGCAAGTCA TAAAAAACCA AAACTACCAA CCAACTTACA  2400
 Q  A  L   G  G  H  R   A  S  H   K  K  P   K  L  P  T   N  L  E
AGAGAAAAAT TCAAAGCCAA TTGAACATGT TGAGAATTGT TCCAAGTCGA ACGAGGATCA  2460
 E  K  N   S  K  P  I   E  H  V   E  N  C   S  K  S  N   E  D  H
TGTCACAACT TTGTCACTTC AAATTTCGAA CAATAATATT AACAACAACA ACAGCAACAA  2520
 V  T  T   L  S  L  Q   I  S  N   N  N  I   N  N  N  N   S  N  N
CAACAACAAC AATAACATCA TCAAGAATAA GAATAGGGTT CATGAATGTT CGATTTGTGG  2580
 N  N  N   N  N  I  I   K  N  K   N  R  V   H  E  C  S   I  C  G
AGCGGAATTT ACTTCAGGGC AAGCATTAGG AGGACACATG AGACGACATA GACCATTACC  2640
 A  E  F   T  S  G  Q   A  L  G   G  H  M   R  R  H  R   P  L  P
AAATAGTATT GCAATTGCAA GTACTAGCCA TGAATTAGAG TCTTCTCATG AAATAAAGAA  2700
 N  S  I   A  I  A  S   T  S  H   E  L  E   S  S  H  E   I  K  N
CACAAGGAAT TTCTTGTCAC TGGACCTTAA TCTACCGGCG CCTGAAGACG ATCATCGGCC  2760
 T  R  N   F  L  S  L   D  L  N   L  P  A   P  E  D  D   H  R  P
AGAAACGAAA TTCTCATTTG CATCAAAAGA ACAAGTCATC GTCTTCTCAG CTTCTCCTTT  2820
 E  T  K   F  S  F  A   S  K  E   Q  V  I   V  F  S  A   S  P  L
GGTTGATTGC CATTACTAAA TCAACACACT GGCCCTTTAT TTATTTTTCG CTATTTTTTT  2880
 V  D  C   H  Y
TTTTTTTGTA TTTCTTGATT TATTTTAATC ATGACACAAT TGTGAATTAT TGTTAACACC  2940
TTATTTTTAT TATTGTACAT TCAACAATTT ATTAATAGAC ATAATTCTTT G            2991
```

FIG. 4
(a)
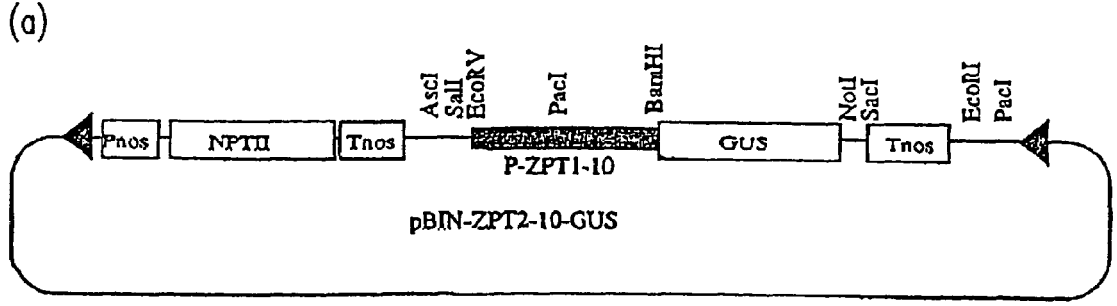
(b)
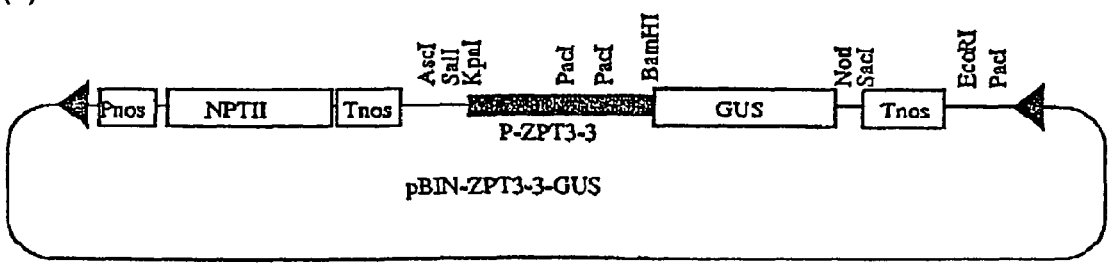
(c)
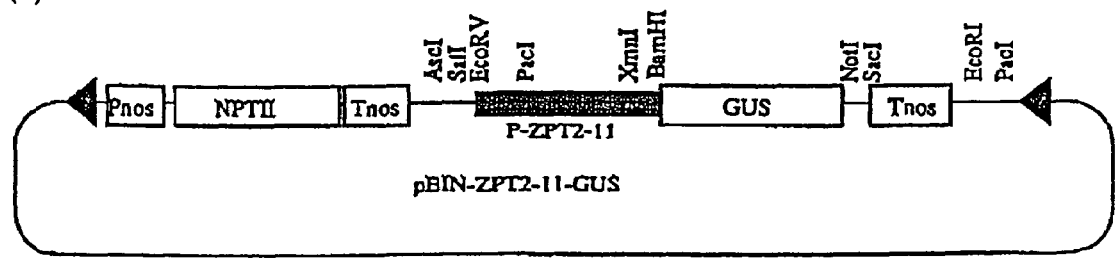

FIG.5
ZPT2-10
(a)
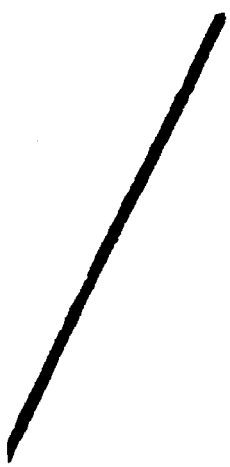
transmitting tissue
Stigma
Style transmitting tissue
Ovary
Placenta surface layer
(b)

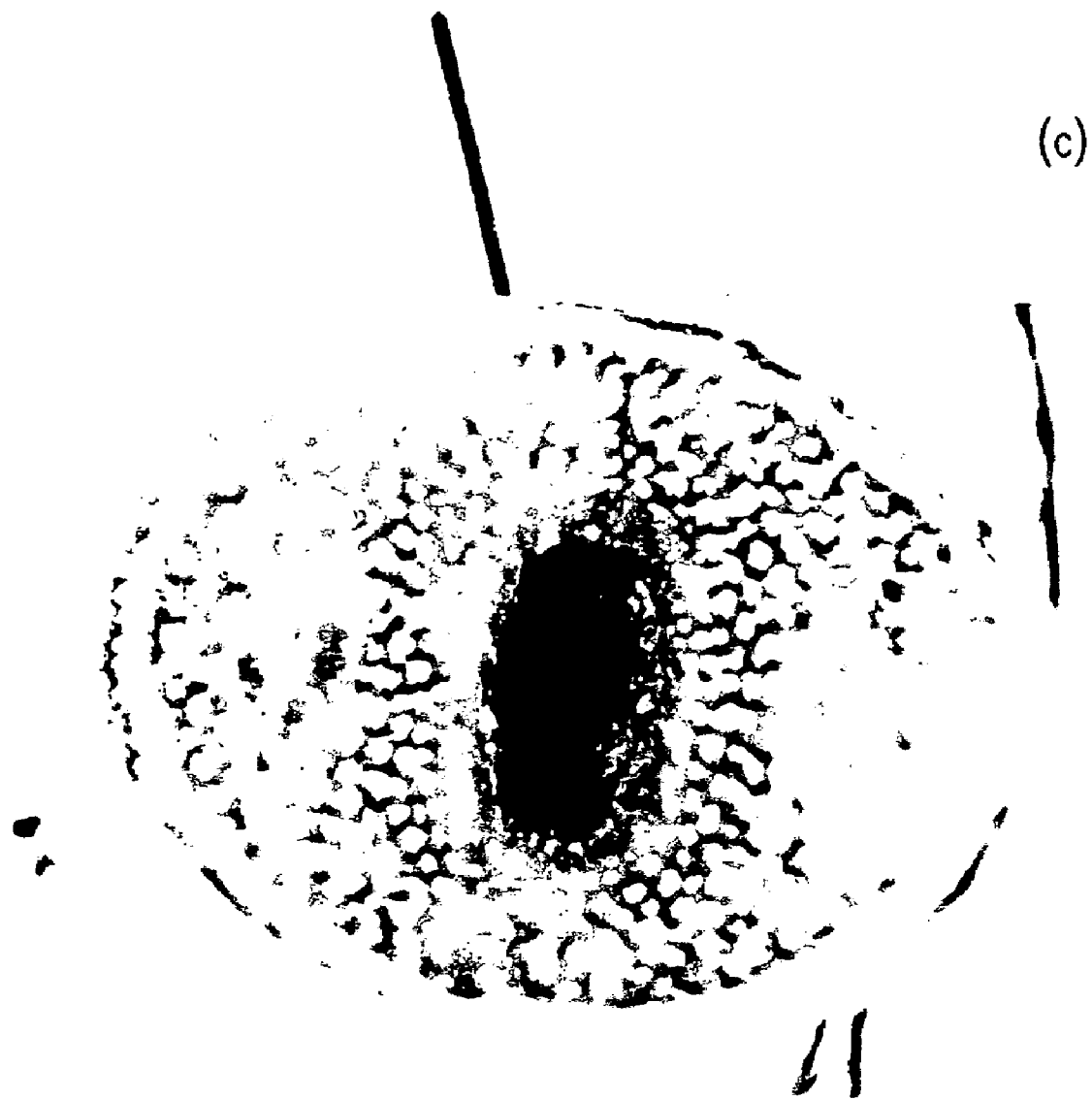

ZPT3-3

(b)

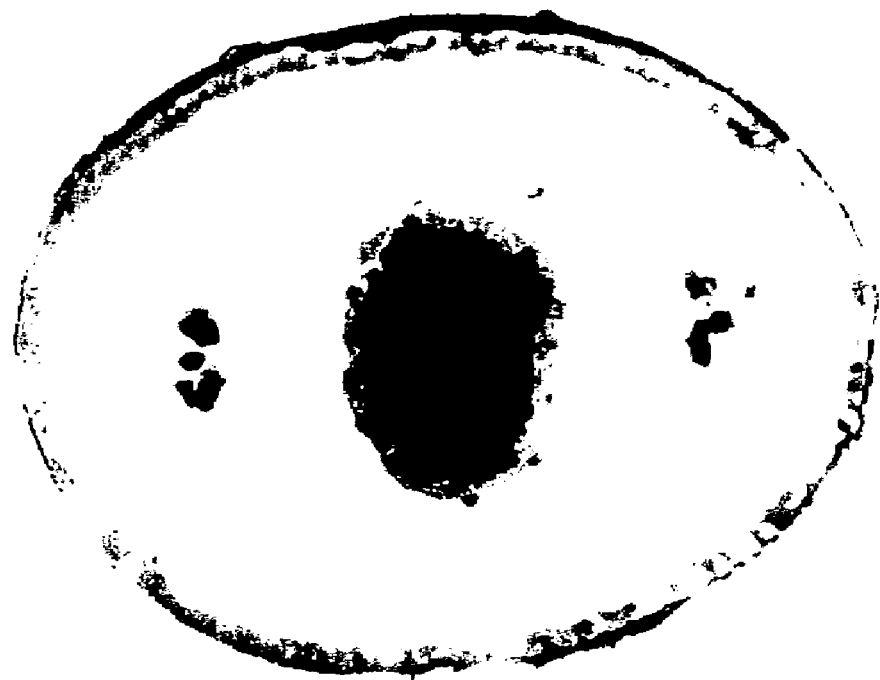
transmitting tissue
(c)
Style (cross-section)

ZPT2-11

(a)

Stigma

Vascular bundle

Style

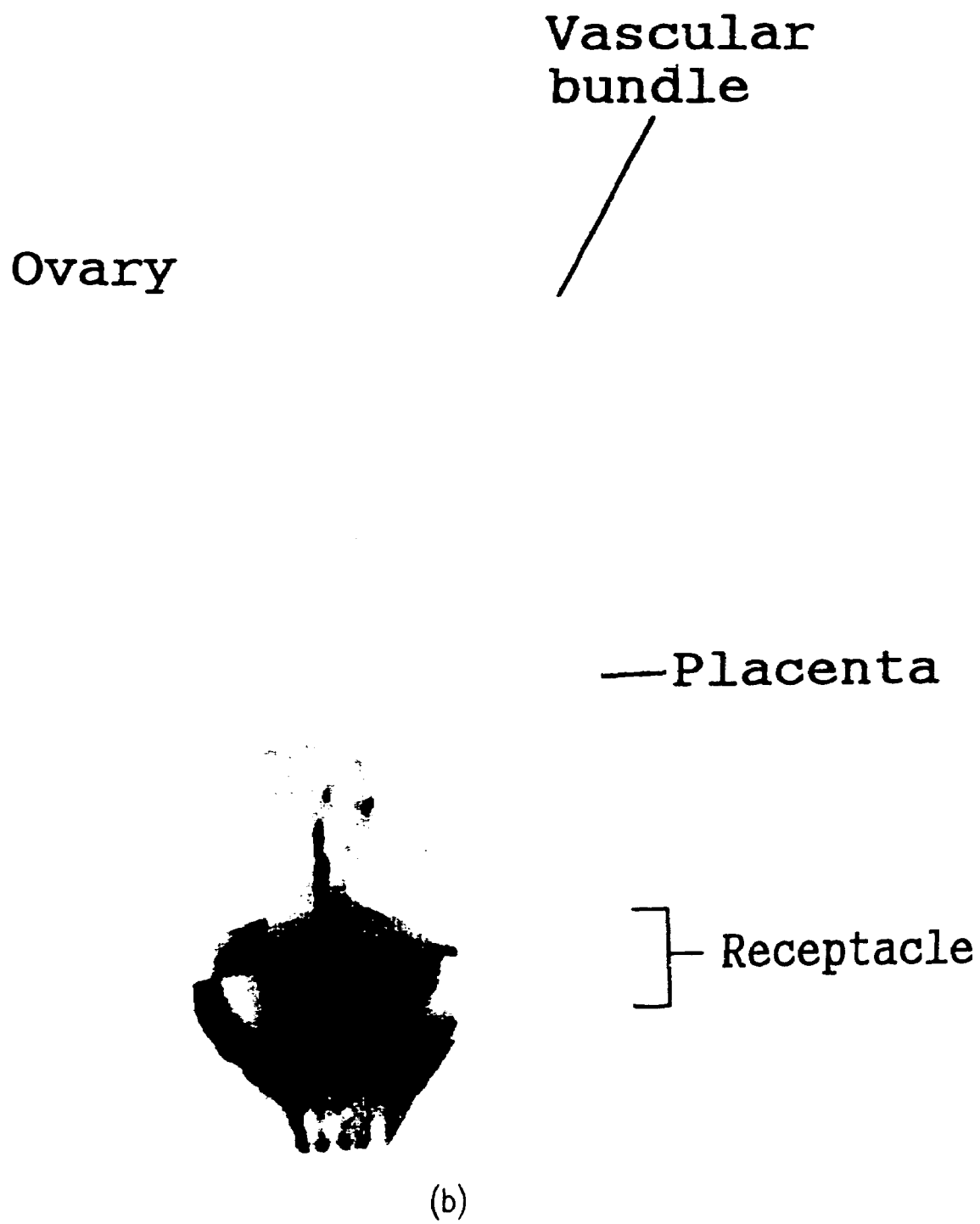

Style(cross-section) (c)
Vascular bundle
Style (enlarged view of cross-section) (d)

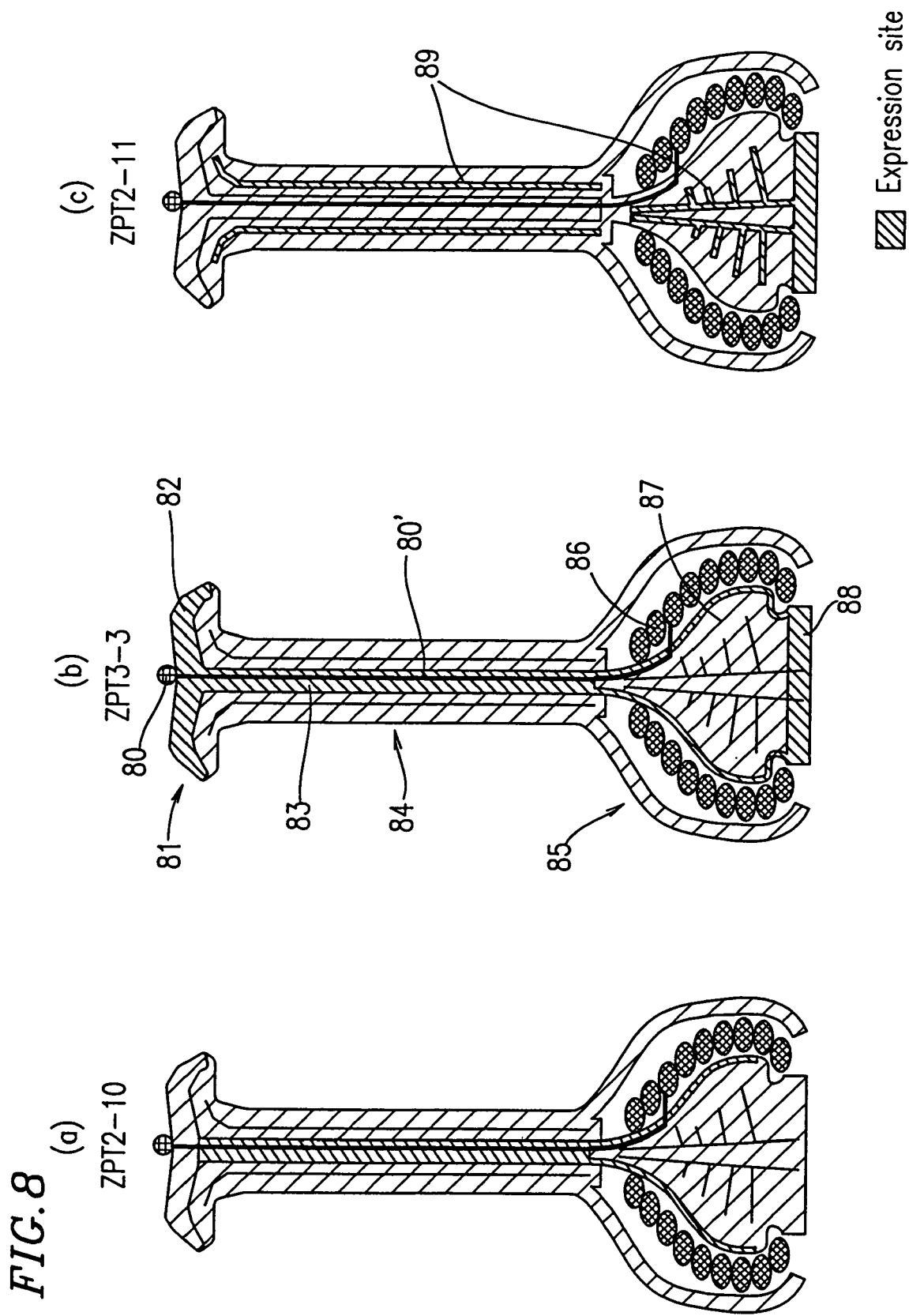

PROMOTER HAVING SPECIFIC ACTIVITY TO PISTIL TISSUE AND USE OF THE SAME

This application claims priority to application no. PCT/JP99/02692 filed 21 May 1999, now publication no. WO 00/71704 published 30 Nov. 2000 which is incorporated herein by reference.

TECHNICAL FIELD

The present invention relates to promoters having an expression activity specific to pistil tissue, and the use of the same. More particularly, the present invention relates to a promoter (ZPT2-10 promoter) for the PEThyZPT2-10 gene, a promoter (ZPT3-3 promoter) for the PEThyZPT3-3 gene, and a promoter (ZPT2-11 promoter) for the PEThyZPT2-11 gene, which are novel promoters derived from *Petunia*, and the use of the same.

BACKGROUND ART

The mechanism for controlling the traits of plants (e.g., morphogenesis of flowers) has been studied in methodologies of molecular biology and molecular genetics using *Arabidopsis* (*Arabidopsis thaliana*), *Antirrhinum* (*Antirrhinum majus*), and *Petunia* (*Petunia hybrida*). Particularly, *Petunia* is often chosen as a research material. The reason is that *Petunia* has great value as a garden plant, there are a number of varieties, it is easy to transform, the flower is large and viewable, and there is a large amount of accumulated genetic knowledge, for example (Hiroshi Takatsuji, "Molecular Mechanism Determining Shapes of Plants", Saibo-kogaku, Syokubutsu-saibo-kogaku Series (Syujyunsya), pp. 96–106 (1994)).

It is considerably important to identify promoters having a tissue-specific expression activity. For example, if a heterogenous gene is desired to be tissue-specifically expressed, an expression cassette is constructed in which the heterogenous gene of interest is linked downstream of a promoter having an expression activity specific to a target tissue (i.e., the heterogenous gene of interest is arranged so as to be expressed under the control of the promoter). The expression cassette is introduced into a plant, allowing specific expression of the heterogenous gene of interest in the target tissue. Specific expression of a heterogenous gene in a plant tissue of interest can confer a modified trait to the plant and therefore has great value in research and horticulture.

For example, when a tissue-specific promoter activity can be found in a pistil tissue, a heterogenous gene can be expressed specifically in the pistil tissue by operatively linking the gene to the promoter and introducing it into a plant. It is believed that, for example, the traits of female sterility and self-incompatibility can be conferred to a plant by utilizing such pistil tissue-specific expression.

It is known that pollination induces synthesis of ethylene which accelerates wilting and shortens the life of flowers. It is also known that generally, pollination cannot induce ethylene synthesis in female-sterile plants and therefore the life of such flowers is long. It is considered that conferring female sterility to flowering plants of garden varieties may lead to an improved lifetime of the flowering plants. Therefore, technology for conferring female sterility to a plant has a great importance to the horticulture industry.

Conventionally, in order to confer the trait of female sterility to a plant, mutation techniques, such as a heavy ion beam irradiation method, have been tried. The following biotechnological methods have also been reported: (1) expression of diphtheria toxin using a promoter specific to the stigma tissue of *Brassica* (Kandasamy, M. K. et al., Plant Cell, 5,263–275 (1993)); and (2) expression of barnase (an enzyme having an activity of causing cell death) using a promoter specific to the stigma tissue of tobacco (Goldman, M. H. et al., EMBO J., 13, 2976–2984 (1994)).

Self-incompatibility is an important trait in terms of the efficiency of crossbreeding. A technique for conferring self-incompatibility to tobacco (*Nicotiana*) has been developed in which a gene having an ability to remove pollen (S-RNase gene) is expressed specifically in the pistil transmitting tissue using a promoter for Chi2;1 derived from tomato (Harikrishna, K. et al., Plant Mol. Biol., 30, 899–911 (1996)).

As described above, the identification of promoters having an expression activity specific to pistil tissue is important not only for scientific research but also for practical applications. If such a promoter can be isolated, it can be very useful for modification of traits of useful plants, such as garden varieties.

DISCLOSURE OF THE INVENTION

The inventor isolated three pieces of DNA from the respective upstream regions of three genes encoding zinc finger-type transcription factors (ZPT2-10, ZPT2-11, and ZPT3-3) (the three pieces of DNA have the DNA sequence from position 1 to 2595 of SEQ ID NO. 1, the DNA sequence from position 1 to 2322 of SEQ ID NO. 2, and the DNA sequence from position 1 to 2012 of SEQ ID NO. 3, respectively), and tested the gene expression control function for these DNA pieces. As a result, the inventor found that these three upstream region DNA pieces have distinct promoter activities specific to pistil tissues, such as a transmitting tissue, a stigma, and a vascular bundle. The present invention was completed based on these findings.

The present invention relates to a promoter comprising:
(a) DNA having a sequence from position 1 to 2595 of a base sequence represented by SEQ ID NO. 1; or
(b) DNA having a part of the sequence of (a) and having a promoter activity specific to at least one of a transmitting tissue and a placenta surface layer.

The present invention also relates to a promoter comprising:
(c) DNA having a sequence from position 1 to 2322 of a base sequence represented by SEQ ID NO. 2; or
(d) DNA having a part of the sequence of (c) and having a promoter activity specific to at least one of a transmitting tissue, a placenta surface layer, a stigmatic secretory zone, and a receptacle.

The present invention further relates to a promoter comprising:
(e) DNA having a sequence from position 1 to 2012 of a base sequence represented by SEQ ID NO. 3; or
(f) DNA having a part of the sequence of (e) and having a promoter activity specific to at least one of a pistil vascular bundle and a pistil receptacle.

The present invention further relates to an expression cassette comprising any one of the above-described promoters and a heterogenous gene operatively linked to the promoter.

The present invention further relates to a method for producing a plant having a modified trait, comprising the steps of introducing the above-described expression cassette into a plant cell; and regenerating the plant cell, into which the expression cassette has been introduced, into a plant body.

The present invention further relates to the use of the expression cassette for modifying a trait of a plant. The expression cassette is introduced to a plant cell. The heterogenous gene operatively linked to the promoter is then expressed.

In one embodiment of this invention, the above-described trait is fertility, and the plant having the modified trait is a female-sterile plant.

In one embodiment of this invention, the above-described trait is compatibility, and the plant having the modified trait is a self-incompatible plant.

In one embodiment of this invention, the above-described plant is a dicotyledon. Preferably, the dicotyledon is a plant of family Solanaceae, and more preferably, a plant of the genus *Petunia*.

In one embodiment of this invention, the above-described heterogenous gene is incorporated into a plant expression vector.

The present invention further relates to a plant having a modified trait which is produced by any one of the above-described methods.

BRIEF DESCRIPTION OF THE DRAWINGS

FIG. 1 is a diagram showing the base sequences of a promoter region, a coding region, and a 3'-untranslated region of a PEThyZPT2-10 (hereinafter referred to as ZPT2-10) genomic gene, and the predicted amino acid sequence of the coding region.

FIG. 2 is a diagram showing the base sequences of a promoter region, a coding region, and a 3'-untranslated region of a PEThyZPT3-3 (hereinafter referred to as ZPT3-3) genomic gene, and the predicted amino acid sequence of the coding region.

FIG. 3 is a diagram showing the base sequences of a promoter region, a coding region, and a 3'-untranslated region of a PEThyZPT2-11 (hereinafter referred to as ZPT2-11) genomic gene, and the predicted amino acid sequence of the coding region.

FIGS. 4(a) through (c) are schematic diagrams showing (a) the structure of a plant expression vector (pBIN-ZPT2-10-GUS) for analyzing a ZPT2-10 promoter, (b) the structure of a plant expression vector (pBIN-ZPT3-3-GUS) for analyzing a ZPT3-3 promoter, and (c) the structure of a plant expression vector (pBIN-ZPT2-11-GUS) for analyzing a ZPT2-11 promoter, respectively. GUS represents a β-glucuronidase gene, Pnos represents a nopaline synthase promoter, Tnos represents a nopaline synthase terminator, and NPTII represents a neomycin phosphotransferase gene, respectively.

FIGS. 5(a) through (c) are photographs showing morphology of (a) the stigma and style, (b) the ovary, and (c) the style (cross-section) of a GUS-stained pistil of a *Petunia* into which pBIN-ZPT2-10-GUS was introduced.

FIG. 8(a) through (c) are diagrams showing expression sites of (a) the ZPT2-10 promoter, (b) the ZPT3-3 promoter, and (c) the ZPT2-11 promoter.

Figure 6:
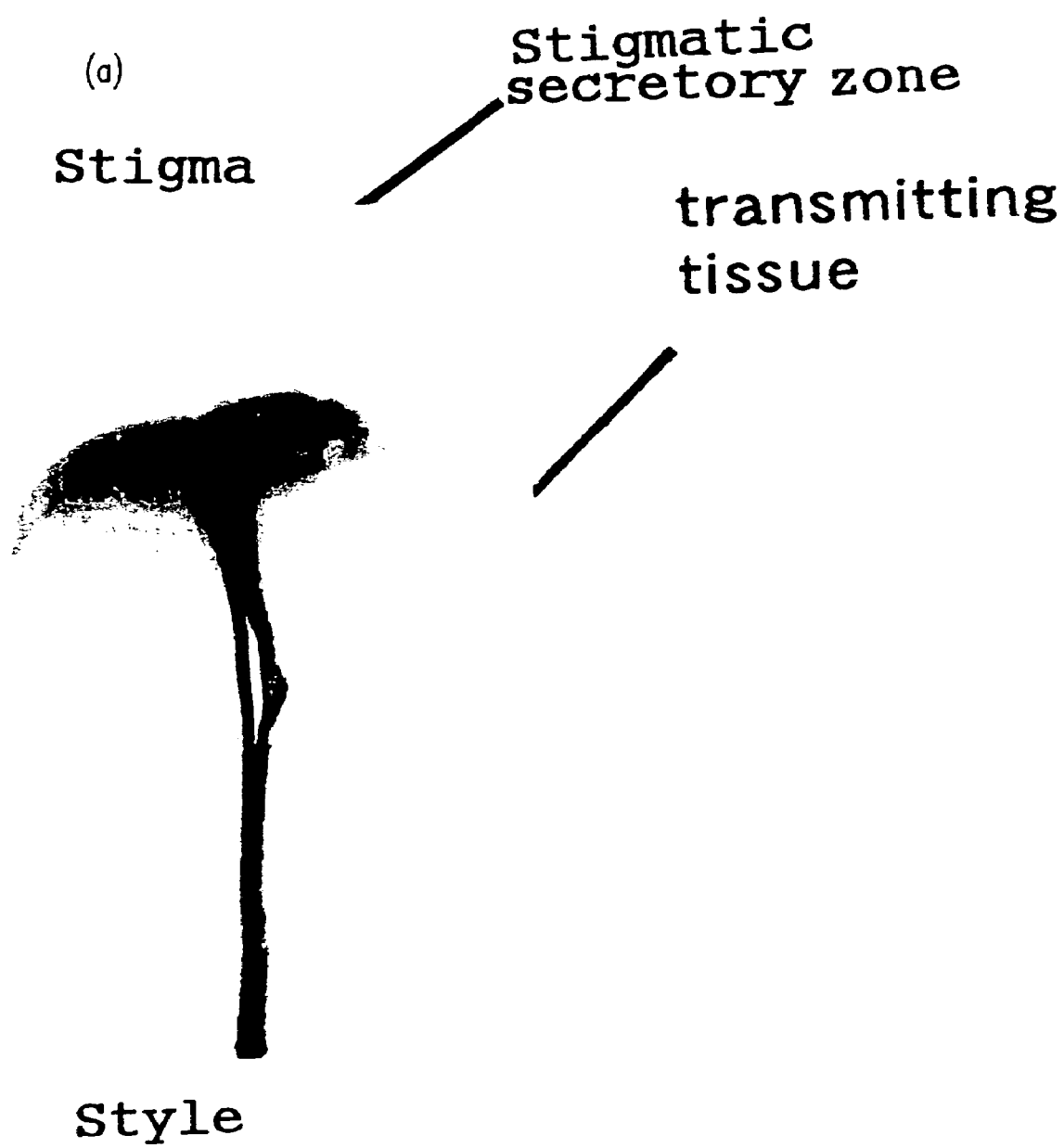
FIGS. 6(a) through (c) are photographs showing morphology of (a) the stigma and style, (b) the ovary, and (c) the style (cross-section) of a GUS-stained pistil of a *Petunia* into which pBIN-ZPT3-3-GUS was introduced.

In the figures, reference numerals indicate, respectively, pollen (80), pollen tube (80'), stigma (81), secretory zone (82), transmitting tissue (83), style (84), ovary (85), ovule (86), placenta (87), receptacle (88), and vascular bundle tissue (89). The expression site of each promoter is hatched with thick slanting lines.

BEST MODE FOR CARRYING OUT THE INVENTION

The present invention will be described in more detail below.

A promoter having an expression activity specific to pistil tissue according to the present invention may include any of the following DNA:
(a) DNA having a sequence from position 1 to 2595 of a base sequence represented by SEQ ID NO. 1;
(b) DNA having a part of the sequence of (a) and, when expressed in a plant, having a promoter activity specific to at least one of a transmitting tissue and a placenta surface layer;
(c) DNA having a sequence from position 1 to 2322 of a base sequence represented by SEQ ID NO. 2;
(d) DNA having a part of the sequence of (c) and, when expressed in a plant, having a promoter activity specific to at least one of a transmitting tissue, a placenta surface layer, astigmatic secretory zone, and a receptacle.
(e) DNA having a sequence from position 1 to 2012 of a base sequence represented by SEQ ID NO. 3; or
(f) DNA having a part of the sequence of (e) and, when expressed in a plant, having a promoter activity specific to at least one of a pistil vascular bundle and a pistil receptacle.

Preferably, a promoter according to the present invention may include any of the following DNA:
(a) DNA having a sequence from position 1 to 2595 of a base sequence represented by SEQ ID NO. 1;
(b)' DNA having a part of the sequence of (a) and, when expressed in a plant, having a promoter activity specific to a transmitting tissue and a placenta surface layer;
(c) DNA having a sequence from position 1 to 2322 of a base sequence represented by SEQ ID NO. 2;
(d)' DNA having a part of the sequence of (c) and, when expressed in a plant, having a promoter activity specific to a transmitting tissue, a placenta surface layer, a stigmatic secretory zone, and a receptacle;
(e) DNA having a sequence from position 1 to 2012 of a base sequence represented by SEQ ID NO. 3; or
(f)' DNA having a part of the sequence of (e) and, when expressed in a plant, having a promoter activity specific to a pistil vascular bundle and a pistil receptacle.

Particularly preferable promoters of the present invention are promoters for the ZPT2-10, ZPT2-11, and ZPT3-3 genes encoding a zinc finger-type transcription factor of *Petunia*. These promoters are DNA having the sequence from position 1 to 2595 of SEQ ID NO. 1, the sequence from position 1 to 2322 of SEQ ID NO. 2, and the sequence from position 1 to 2012 of SEQ ID NO. 3, respectively.

A sequence, which has promoter activity specific to at least one pistil tissue, and is in a promoter region for the ZPT2-10, ZPT2-11, or ZPT3-3 gene, and which is obtained by removing a sequence non-essential for tissue-specific expression activity, is within the scope of the present invention. Such a sequence may be obtained by deletion of part of a promoter according to a commonly used method. Briefly, plasmids fusing various deletion mutants of the promoter regions for the ZPT2-10, ZPT2-11, and ZPT3-3 genes (e.g., mutants obtained by deleting the promoter regions for the ZPT2-10, ZPT2-11, and ZPT3-3 genes from the respective 5'-upstream portions in various lengths) with an appropriate reporter gene (e.g., the GUS gene) are used to measure the tissue-specific promoter activities of the deletion mutants, whereby a region(s) essential for the activities can be identified.

Once a region essential for a promoter activity is identified, the expression activity of the promoter may be enhanced or the expression specificity to a tissue may be modified by further modifying the sequence of the region or adjacent regions. Any resultant variant is within the scope of the present invention as long as it has promoter activity specific to at least one pistil tissue.

The term "tissue-specific promoter activity" as used herein refers to the ability of a promoter to be expressed specifically in any certain tissue in a naturally-occurring plant or in a plant into which an expression cassette including the promoter has been introduced. Here, the term "specifically" refers to that the expression activity of the promoter is higher in the certain tissue than in at least one of the other tissues in the same plant body. The level of the expression activity of a promoter may be assessed by comparing the expression level of a promoter in a predetermined tissue with that in other tissues using a commonly used method. The expression level of a promoter is typically determined by the amount of production of gene products expressed under the control of the promoter. The term "tissue-specific expression activity" of a promoter and the term "tissue-specific promoter activity" as used herein have the same meaning.

A promoter having an expression activity specific to at least one pistil tissue is within the scope of the present invention.

Examples of pistil tissues include a transmitting tissue, a placenta surface layer, astigmatic secretory zone, a receptacle, and a pistil vascular bundle, and the like (see FIG. 8). A transmitting tissue and a placenta surface layer are elongation paths through which a pollen elongates a pollen tube after pollination to reach the ovule. A stigmatic secretory zone is a region to which pollen is attached. A receptacle is a distal end of the peduncle which bears a flower and a leaf. A pistil vascular bundle system is speculated to play an important role, for example, in supplying substances required for the function of the pistil in the stigmatic secretory zone (e.g., a secretion product required for attachment of pollen, a filling compound for accelerating extension of a pollen tube in the elongation path of the pollen tube, and nutrients for the style and stigma).

The term "modification" as used herein with respect to a trait of a plant refers to that a trait which a plant has not had before transformation (a wild type or a garden variety) is conferred to the plant after transformation, or that the level of a plant trait which a plant has had before transformation (a wild type or a garden variety) is increased or decreased. Such trait modification may be obtained as follows: a heterogenous gene operatively linked to a promoter according to the present invention is introduced into a plant; and in such a transformed plant, the heterogenous gene is tissue-specifically expressed under the control of the promoter of the present invention. The level of the trait modification may be assessed by comparing a trait of a plant (a wild type or a garden variety) after transformation with that before the transformation.

Examples of a preferable trait to be modified include, but are not limited to, female sterility, self-incompatibility, and insect-pest resistance.

The promoter of the present invention may be obtained by screening a plant genomic library using known cDNA as a probe and isolating a corresponding genomic clone, for example. Examples of such cDNA include cDNA of *Petunia*-derived zinc finger-type transcription factors ZPT2-10, ZPT2-11, and ZPT3-3.

Methods for preparing a genomic library, stringent conditions for hybridization with a probe, and methods for gene cloning, are known to those skilled in the art. For example, see Maniatis et al., "Molecular Cloning", A Laboratory Manual, 2nd Ed., Cold Spring Harbor Laboratory Press, Cold Spring Harbor, N.Y. (1989).

The base sequence of the resultant gene may be determined by a method for analyzing a nucleotide sequence, which is known in the art, or using a commercially available automatic sequencer.

The promoter of the present invention is not limited to an isolated naturally-occurring promoter and may include a synthesized polynucleotide. A synthesized polynucleotide may be obtained by synthesizing or modifying the sequence or activity region of a promoter which has been sequenced as described above using a method well known to those skilled in the art.

The promoter of the present invention may be operatively linked to a desired heterogenous gene to produce an expression cassette using a method well known to those skilled in the art. The expression cassette may be introduced into a plant cell using a known recombinant technique. The introduced expression cassette is incorporated into the DNA of the plant cell. The DNA of the plant cell includes not only a chromosome, but also DNA contained in various organelles in a plant cell (e.g., mitochondria and chloroplasts).

The term "plant" as used herein includes either monocotyledons or dicotyledons. Preferable plants are dicotyledons. Dicotyledons include Archichlamiidae and Sympetalidae. A preferable subclass is Sympetalidae. The subclass Sympetalidae includes Gentianales, Solanales, Lamiales, Callitrichales, Plantaginales, Campanulales, Scrophulariales, Rubiales, Dipsacales, and Asterales. A preferable order is Solanales. The order Solanales includes Solanaceae, Hydrophyllaceae, Polemoniaceae, Cuscutaceae, and Convolvulaceae. A preferable family is Solanaceae. The family Solanaceae includes *Petunia, Datura, Nicotiana, Solanum, Lycopersicon, Capsicum, Physalis,* and *Lycium*. A preferable genus is *Petunia, Datura,* and *Nicotiana*, and more preferably, *Petunia*. The genus *Petunia* includes *P. hybrida, P. axillaris, P. inflata, P. violacea,* and the like. A preferable species is *P. hybrida*. The term "plant" refers to a plant body including a flower and a seed obtained from the plant body, unless otherwise specified.

Examples of the "plant cell" include cells of tissues in plant organs, such as a flower, a leaf, and a root; callus; and suspension culture cells.

The term "expression cassette" as used herein refers to a nucleic acid sequence including the promoter of the present invention and a heterogenous gene operatively linked to the promoter (i.e., in frame).

The term "heterogenous gene" as used herein refers to any of the following genes: an endogenous gene in *Petunia* other than the ZPT2-10 gene, ZPT2-11 gene, and ZPT3-3 gene; an endogenous gene of another plant; or a foreign gene derived an organism other than a plant (e.g., a gene derived from an animal, an insect, a bacterium, and fungus). The expression of the gene product is desired in any of pistil tissues.

The term "plant expression vector" refers to a nucleic acid sequence including various regulatory elements, which are linked thereto in such a manner as to be operative in a cell of a host plant, in addition to a promoter in an expression cassette. Preferably, examples of the regulatory elements include a terminator, a drug-resistance gene, and an enhancer. It is well known to those skilled in the art that the types of plant expression vectors and kinds of regulatory elements used may vary depending on host cells. The plant expression vector used in the present invention may further include a T-DNA region. The T-DNA region plays a role in increasing the efficiency of gene introduction, particularly when *Agrobacterium* is used to transform a plant.

The term "terminator" refers to a sequence which is positioned downstream of the region of a gene encoding a protein and involves termination of transcription of DNA to mRNA and addition of poly-A sequence. It is known that a terminator contributes to the stability of mRNA and has an influence on the expression amount of a gene. Examples of a terminator include, but are not limited to, the CaMV35S terminator and the terminator (Tnos) for the nopaline synthase gene.

A preferable "drug-resistance gene" facilitates screening of transformed plants. Preferably, examples of a drug-resistance gene include, but are not limited to, the neomycin phosphotransferase II (NPTII) gene for conferring kanamycin-resistance and the hygromycin phosphotransferase gene for conferring hygromycin-resistance.

An "enhancer" can be used to increase the expression efficiency of a gene of interest. An example of a preferable enhancer includes an enhancer region including an upstream sequence of the CaMV35S promoter. A plurality of enhancers can be used for a single plant expression vector.

The plant expression vector of the present invention may be produced by a gene recombinant technique well known to those skilled in the art. To construct a plant expression vector, for example, pBI type vectors or pUC type vectors may be preferably used, but the present invention is not limited to these vectors.

Methods well-known to those skilled in the art for introducing a plant expression vector into a plant cell includes, for example, a method mediated by *Agrobacterium* or a method of directly introducing the vector into the cell. An example of a method mediated by *Agrobacterium* includes a method developed by Nagel et al. (FEMS Microbiol. Lett., 67, 325 (1990)). In this method, *Agrobacterium* is first transformed using a plant expression vector (e.g., by electroporation), and the transformed *Agrobacterium* is then introduced into a plant cell using a well-known method, such as a leaf disk method. Examples of a method for directly introducing a plant expression vector into a cell include an electroporation method, a particle gun method, a calcium phosphate method, and a polyethylene glycol method. These methods are well known in the art. A method suitable for the plant to be transformed can be selected from these methods by those skilled in the art.

Cells into which a plant expression vector has been introduced are selected with reference to drug-resistance, such as kanamycin-resistance. A selected cell may be reproduced into a plant body using a commonly used method.

In a regenerated plant body, expression of a heterogenous gene of interest may be confirmed using a method well known to those skilled in the art. This may be conducted, for example, by northern blotting analysis. Specifically, all RNAs are extracted from a tissue in which the promoter of the present invention is specifically expressed, are subjected to denaturated-agarose electrophoresis, and are blotted onto an appropriate membrane. The blotted membrane is subjected to hybridization using a labeled RNA probe which is complementary to a part of the heterogenous gene of interest. Thus, an mRNA of the heterogenous gene of interest can be detected. When the heterogenous gene is endogenous to the transformed plant, the amount of mRNA of the heterogenous gene of interest in a tissue, in which the promoter of the present invention is expressed specifically, can be compared with the amount of mRNA of the heterogenous gene of interest in the same tissue of an untransformed control plant, thereby assessing a change in the amount of expression of the heterogenous gene of interest.

The tissue-specific expression activity of the promoter of the present invention may be confirmed using the above-described method. For example, the GUS activity distribution of a plant transformed using an expression vector, to which the promoter of the present invention and the GUS gene are operatively linked, can be tested using a commonly used a histochemical staining method, thereby identifying the tissue-specific expression activity of the promoter.

A plant according to the present invention is a plant which is transformed using a heterogenous gene of interest operatively linked to the promoter of the present invention by the above-described method. In the plant, the heterogenous gene of interest is tissue-specifically expressed under the control of the promoter of the present invention, resulting in modification of a trait of the plant. Examples of a trait to be modified include, but are not limited to, fertility, compatibility, and insect-pest resistance.

According to the present invention, a practical promoter derived from a *Petunia* gene, which has an expression activity specific to pistil tissues, is provided. The promoter of the present invention may be used to modify a trait of a plant. For example, under the control of this promoter, a gene product which can injure any of pistil tissues (e.g., the transmitting tissue, the placenta surface layer, the stigmatic secretory zone, the receptacle, and the pistil vascular bundle) is expressed specifically in the tissue (e.g., an enzyme having an activity which causes cell death), whereby the tissues may be destroyed and the reproductive function of the pistil may be inhibited. As a result, the plant may be given a trait of female sterility. Alternatively, a gene having a function of removing pollen of a specific gene type (e.g., the S-RNase gene) may be expressed in an appropriate tissue, particularly the transmitting tissue. As a result, a plant may be given a trait of self-incompatibility. Alternatively, a protein having an anti-insect-pest activity may be expressed in the stigma, thereby making it possible to produce an insect-pest resistance plant which can kill or repel an insect pest contacting the stigma.

EXAMPLES

Hereinafter, the present invention will be described by way of examples. The scope of the present invention is not limited only to these examples. Restriction enzymes, plasmids, and the like used in the examples are available from commercial sources.

Example 1

Isolation of the ZPT2-10 Promoter Region and Ligation to the GUS Reporter Gene cDNA of ZPT2-10 (Kubo, K. et al., Nucleic Acids Research, 26, 608–616 (1998)) was labeled with [$\alpha$-$^{32}$P] dCTP using a typical random primer method (Sambrook et al., supra) to produce a radioisotope-labeled probe. A genomic library for *Petunia* (*Petunia hybrida* var. *Mitchell*) produced in the EMBL3 vector (manufactured by Stratagene) was screened using the labeled probe. From the resultant clones, a genomic DNA fragment of about 3.0 kb including a upstream region of the gene was subcloned into an EcoRV-XbaI site in pBluescriptSK vector and was subcloned (pBS-ZPT2-10EX), followed by sequencing of the base sequence of the genomic DNA fragment (SEQ ID NO. 1) (see FIG. 1). Thereafter, such a plasmid was used as a template to conduct PCR where a primer including a BamHI recognition sequence (CCGGGGATCCATCATCTTGTA-GAAGATCCAT; SEQ ID NO. 4) and a commercially available M13-20 primer were used. Therefore, the BamHI site was introduced immediately downstream of the translation initiation point of the ZPT2-10 protein (position 2595 of the base sequence shown in FIG. 1). DNA fragments produced by the PCR were cleaved at EcoRV and BamHI sites, and the resultant restriction fragments were cloned in the pBluescript vector, followed by sequencing of the fragments. Thereafter, the cloned vectors were cleaved with SalI and BamHI. The resultant DNA fragments were inserted upstream of the GUS coding region of commercially available pUCAPGUSNT (pUCAP-ZPT2-10-GUS-NT). Therefore, the GUS region was linked in frame to a region in the vicinity of the N-terminus of the coding region of the ZPT2-10 gene. Further, DNA fragments (including the promoter, GUS, NOS, and terminator of ZPT2-10) obtained by cleaving pUCAP-ZPT2-10-GUS-NT with AscI and EcoRI were inserted into pBINPLUS vector to obtain pBIN-ZPT2-10-GUS (FIG. 4a).

Example 2

Isolation of the ZPT3-3 Promoter Region and Ligation to the GUS Reporter Gene Similar to Example 1, the genomic DNA of ZPT3-3 was isolated. A DNA fragment (KpnI-EcoRI) of about 2.5 kb including an upstream region of the ZPT3-3 gene was subcloned into the pBluescriptSK vector (pBS-ZPT3-3-KE). Thereafter, the base sequence of the DNA fragment was determined (SEQ ID NO. 2) (see FIG. 2). The plasmid was used as a template to conduct PCR where a primer including a BamHI recognition sequence (CCGGGGATCCACAT-GACTTGTGTTTCTCCAT: SEQ ID NO. 5) and a commercially available M13-20 primer were used, whereby a BamHI site was introduced immediately downstream of the translation initiation point of the ZPT3-3 protein (position 2322 of the base sequence shown in FIG. 1). Ligation of the thus-obtained DNA fragments was conducted so that ZPT3-3 and GUS were in frame. In a similar manner to Example 1, pBIN-ZPT3-3-GUS was produced (FIG. 4b).

Example 3

Isolation of the ZPT2-11 Promoter Region and Ligation to the GUS Reporter Gene Similar to Example 1, the genomic DNA of ZPT2-11 was isolated. A DNA fragment (EcoRV-EcoRI) of about 2.1 kb including an upstream region of the ZPT2-11 gene was subcloned into the pBluescriptSK vector (pBS-ZPT2-11-EE). Thereafter, the base sequence of the DNA fragment was determined (SEQ ID NO. 3) (see FIG. 3). The plasmid was used as a template to conduct PCR where a primer including a BamHI recognition sequence (CCGGGGATCCTTCTTG-CATTTGAACTTCCAT; SEQ ID NO. 6) and a commercially available M13-20 primer were used, whereby a BamHI site was introduced immediately downstream of the translation initiation point of the ZPT2-11 protein (2012-position of the base sequence shown in FIG. 1). Ligation of the thus-obtained DNA fragments was conducted so that ZPT2-11 and GUS were in frame. In a similar manner to Example 1, pBIN-ZPT2-11-GUS was produced (FIG. 4c).

Example 4

Introduction of a Fused Gene of the ZPT2-10, ZPT3-3, or ZPT2-11 Promoter and GUS into *Petunia*

(1) *Agrobacterium tumefaciens* LBA4404 strain (CLON-TECH Laboratories Inc., Palo Alto, Calif.) was cultivated in L medium containing 250 µg/ml of streptomycin and 50 µg/ml of rifampicin at 28° C. In accordance with Nagel et al.'s method (supra), a cell suspension was prepared. Electroporation was conducted in the cell suspension to introduce each of the plasmid vectors constructed in Examples 1, 2, and 3 into the strain, respectively.

(2) A polynucleotide encoding a fused gene of the ZPT2-10, ZPT3-3, or ZPT2-11 promoter and GUS was introduced into a *Petunia* cell using the following method. The transformed *Agrobacterium tumefaciens* LBA4404 strain obtained in procedure (1) was cultivated with shaking in YEB medium (DNA Cloning, Vol. 2, p. 78, D. M. Glover Ed., IRL Press, 1985) (28° C., 200 rpm). Thereafter, the resultant culture medium was diluted by a factor of 20 with sterilized water. The diluted medium was co-cultured with a piece of a leaf of *Petunia* (*Petunia hybrida* var. *Mitchell*). After 2 to 3 days, the leaf piece was cultured in a medium containing an antibiotic, thereby removing the above-described bacterium. The leaf piece was subcultured in a selective medium on a two week basis. A transformed *Petunia* cell was selected with reference to the presence or absence of kanamycin resistance due to the expression of the NPTII gene derived from pBINPLUS which was introduced along with the above-described three fused gene. The selected cell was introduced into a callus using a commonly used method, followed by redifferentiation into a plant body.

Example 5

Tissue Specificity of the Activity of the ZPT2-10 Promoter

A fused gene of the upstream region of the ZPT2-10 gene and GUS was introduced into a plant. The flower of the resultant transformant was assessed as to the distribution of GUS activity using X-GUS as a substrate (Gallagher, S. R. (Ed.) GUS protocols: using the GUS gene as a reporter of gene expression, Academic Press, Inc., San Diego (1992)). As a result, GUS activity was detected specifically in a cell layer of the transmitting tissue of the style and the uppermost layer of the placenta (i.e., the placenta surface layer) of the pistil (FIGS. 5 and 8(a)).

Example 6

Tissue Specificity of the Activity of the ZPT3-3 Promoter

A fused gene of the upstream region of the ZPT3-3 gene and GUS was introduced into a plant. The flower of the resultant transformant was used to assess the distribution of the GUS activity as in Example 5. As a result, the GUS activity was detected specifically in the stigmatic secretory tissue, the transmitting tissue of the style, the placenta surface layer, and the receptacle of the pistil (FIGS. 6 and 8(b)).

Example 7

Tissue Specificity of the Activity of the ZPT2-11 Promoter

Figure 7:
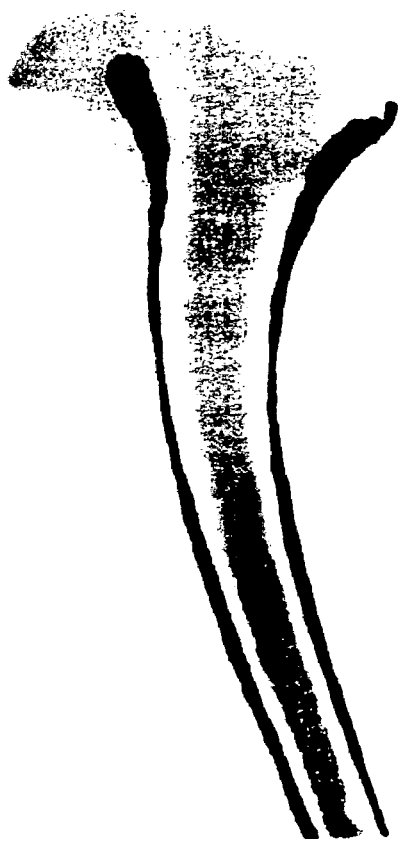
FIGS. 7(a) through (c) are photographs showing morphology of (a) the stigma and style, (b) the ovary, and (c) the style (cross-section; (d) its enlarged view) of a GUS-stained pistil of a *Petunia* into which pBIN-ZPT2-11-GUS was introduced.

A fused gene of the upstream region of the ZPT2-11 gene and GUS was introduced into a plant. The flower of the resultant transformant was used to assess on the distribution of the GUS activity as in Example 5. As a result, the GUS activity was detected specifically in the vascular bundle tissue ranging from the stigma to the style and the placenta of the pistil, and the receptacle (FIGS. 7 and 8(c)).

INDUSTRIAL APPLICABILITY

The *Petunia*-derived ZPT2-10, ZPT2-11, and ZPT3-3 promoters of the present invention exhibit a promoter activity specific to pistil tissue. These promoters are useful for modification of a trait of a plant by genetically engineering pistil tissues.

The invention claimed is:

1. An isolated promoter comprising:
DNA having the sequence from position 1 to 2012 of SEQ ID NO. 3.

2. A plant expression cassette comprising the promoter of claim 1 and a heterogenous gene operatively linked to the promoter.

3. A method for producing a plant having a modified trait, comprising the steps of: introducing the expression cassette of claim 2 into a plant cell; and regenerating the plant cells, into which the expression cassette has been introduced, into a plant body.

4. The method of claim 3, wherein the trait is fertility, and the plant having the modified trait is a female-sterile plant.

5. The method of claim 3, wherein the trait is compatibility, and the plant having the modified trait is a self-incompatible plant.

6. The method of claim 3, wherein the plant is a dicotyledon.

7. The method of claim 6, wherein the plant is a plant of the family Solanaceae.

8. The method of claim 7, wherein the plant is a plant of the genus *Petunia*.

9. The method of claim 3, wherein the expression cassette is incorporated into a plant expression vector.

10. A plant having a modified trait which is produced by the method of any one of claims 3 to 9.

* * * * *

SEQUENCE LISTING

<160> NUMBER OF SEQ ID NOS: 9

<210> SEQ ID NO 1
<211> LENGTH: 3723
<212> TYPE: DNA
<213> ORGANISM: Petunia hybrida

<400> SEQUENCE: 1

```
gatatcgctt cactaccgtc tgttggtggc ccaatgacat ttaggggtc ggcgaaatta         60 actatttcac caccaatgat cacggtggtg gtggtggtgg cggcagcagg aatttcatcg        120
ccagaatggc tgctagagtt ctgagcagaa ttggtggcag acttcttctt tttttacaaa       180
gaagcttgtg attacgactt taattataga tttcaataag cacaaatagg aatttctctt        240
gcttcgaaat tgctacagtt ggaataagat aaagtaaaaa tggtggtgtg attaagtggg        300
catttatatg tgagaagtca tcattgtctt gggaaggagg acgaaatggc gcaacctttc       360
caacggtcgc cgcgtgtaac ggatgggaag gtgaagcgat ggctaccttt ttgaattact        420
tggcacacga gcagccacac cacttctccc gcttgttttt cattccactc ctcgggcact        480
ctggcaattg ctcgaggagt aggggacta tctgtactgg gcaaaatatg atttgcacac         540
gtagccgccg aagcataaag ttcgggatac tttttgcaag attcacaagt tggatgaggt        600
agcgacatgg cttccgaagc gaagcctcag gatcgagatc atttgtaagc gtcgtaatat        660
gatcgcttca gagaacaggc agttcatcgc cctaaggtga aatgatctta acctcaggag        720
gatagttcgg ctacagcgta agaggcgccc catgatctcc gcccagtatc tcagcattta        780
acgggtaaga tttggggcag accacaattt agatagagtg ggctaattaa tgcccttaat        840
tgtcactaac atatggtcta taagtaaaat tcattttatc ttgtaaagat attcacaaat        900
ttataggcaa tactctgccc aattgtaatc tcaaggcatt catattgaaa tcgttacttt        960
gtgctcttat tgtccattca tttccattaa tttcttgtcc tttaccaact ttgatacatc       1020
aaattatttg taaaatataa attcaattat ttccctactc cgatttagag aaatataatt       1080
actactatag attaaaatac aaatttacat tatcaaaata aatctaacaa agtacacata       1140
aacaagcttg taaaagtaag cgtgtggaaa tggggatcta acaaaaagca tgatgcacga       1200
ctaggtcctt tcttttttcc cccaacaaga cgcgatgcat ttacttccct agaaaactcc       1260
```

-continued

```
tttttcaaac gaataggatg agaacgttag taatttcctc cctagcaacc cccacccatg      1320
acccatcatc tttcattccc aatcagagaa aaaatttagc tcaagatcct taattaaagg      1380
acattataat ttccaaatta tttattattc cttcgctgtt ataaagatat aataaaaacg      1440
tatgaaagtt cagccaacgt attaaataag atgccacaat tttgtggtcg gcccagccag      1500
caccatgcca aaattttcac ctcctagcct tgtagtggaa aattttatcc atccaccaca      1560
tcctcgactg agaatcgaca tcacaagcac aagcaaagat tcactagtgg agcttcctcc      1620
aggtaaagag ggggttactt tggtggttgg tcatacccaa tttaaacaca tgacatacat      1680
acatacatac agtggcttgg tgtaaaaaaa ttttgtgggt aagtttttag tacaatttat      1740
ttgtctccgt ccttaattca ataccagcag ttttgttgac tgtttacgaa attaagttaa      1800
actaaattta atatcctaac ctctttctt tttttctt tttttataat ggtttaatta      1860
caaattcttg gcaaagagtg atgtaatctt tagcaaagca tagagtattt tatgtgatcc      1920
tttttcatat aataagaggg aaacgtattt aaaggcccaa gttaacagag gatagaaagg      1980
attatatcaa gtttgatccg atatacaatc cagtattta tttatataat ccagtataat      2040
acgtcaaatt ataccgtcat tgtaaaatta ttgtcaaata cattaactta aacccttat      2100 taaattaccc cgcataacat gtgtagggtt atttaggaaa agtagagatg ggattgaact      2160
aaatgcaaag ctcgcatgtt acatgttgtt cccttctact ctcttttcta tctttgcctt      2220
tatgcatacg ttttaattga gttttctta ttaattgcat atttccgttt taaagaaaat      2280
tacttccaat taattcagaa tctaactttc tcttaaatgt ttttttttc tgttgtaaaa      2340 atgtcatccc ttaaatattc ttgctctta tattcttggt gcaggaagag tgctcgtcac      2400
atactttaaa acaattcaga gtatttgcaa gaacaaaaca cggacaacac acagcaaatt      2460
agtgaagaaa cagactcaat tccctcaatt tcatcatccc cagaagatga agagaatgcg      2520
aagaaaaaga tattgaatta taggatcaga gtgaatccaa agaagagcct tagaattatg      2580
gatcttctac aagatagaga gagtgaaacc gagtcattac catatccaac acaatgtaaa      2640
cgatacaagc ggatcataaa ctcaagaatc tcagatacac attacaatca gtttttatca      2700
ttagaacgac gacgacaaca acaacaacaa cagtatggaa agattacaga gtttccattt      2760
gttgagtctg agccagtgag ttcaatttca gacacttcac cagatgaaga cgttgcgaac      2820
tgcttgatga tgttatctag agataagtgg atgacacaag aaaatgaagt tatcgacaat      2880
agtgctagct atgatgaaga tgtaaaaaca gaggactctg tagttgttaa agtgacaacg      2940
actaggaggg gtagaggtaa gtacatatgt gaaacatgta caaagttttt tagatcttat      3000
caagcacttg gtggtcatag agcaagtcac aagaagatta aagtctcaat taatgaaaca      3060
aaaaacaatg gaaatgtaga aagtgaggtt caaaaggata aaatacatga atgtcctgtt      3120
tgttacagag tattttcatc aggacaagct cttggtggac acaagaggtc acatggtatt      3180
ggtgtagcag ccacaaatgt gagtctttca acaaaaattg tatcatcaag aattagtgga      3240
actatgatag atctcaatat tcctgctaca ttggaggatg atgagattag tcaaattgag      3300
gtttctgcag tttctgatga tgaatttgtc aacccctgag tcgaaggtct atcagaaaga      3360 accctgtag gagtaagatc tgcgtacatc tcaccctcct cagaattcat ctgtaggatt      3420
atatcaggta cattgttatt gctgttgaat ttgtcatccc catcaagcac tgaaatgatg      3480
ttattcttag agttaatgaa actcaagaat tataggtaaa gttttgttct tattttgacc      3540
tttttaagtt cttaggtatg gaactaagga aattgatcag tacttttct tggaaaacat      3600
```

-continued

```
tagcactttc caagctatac tcattgaata tctgaatagt tttgactgta attaaatttt    3660
ccaactctgc tttgtttatg ttacagctta ttaatatcat ctattaattt aactctgttc    3720
tgt                                                                  3723
```

<210> SEQ ID NO 2
<211> LENGTH: 2651
<212> TYPE: DNA
<213> ORGANISM: Petunia hybrida

<400> SEQUENCE: 2

```
cgaattgggt acgtcgacgt acatgccatt atctttccct tctcttagtc cttgtattgg      60
ataacttct tccattttt aattccaata aacttgtccc ttcaaattat atgttttact       120
tttttaaaat ttagatagtt agtaggaaat gaagactgca actatcaaat aatggagtat     180
gatggatgag acccctccac tatttatgta gcgcaactcg aaattaatct gttcagtaaa     240
tatcgaatac aatatggtta tagaaaaaca aaatacataa agtaagaaaa taagggaca     300
gacaagaact tttcccttg catcgaatag aaaaggaag ataaaaatgg actaacaaat      360
taattacagt tgaaactata agtacgagta aatttcattg acggtcaccc aactttcatg    420
tttgttatcc aaaagttact attatttcat atgttatcca aaatcatttt aactttatttt   480
taagttacat aaaaataatt ttgccatgaa atagcttaat acatgcttga aaatgacttc    540
actagagtac ataattttga ttaaatataa ttaatgtatt aaactcctta cttgacccat    600
attaaaaatc tgactcagtt gtctaaagct catacaaatc ttacacactc aaattattgg    660
gtttagcttt ctattttgtt ctttttattg ttaagtttta ctgtttaagt tattggtata    720
gttattttgt atttcttttt tgtgctatcc ggcgcagtaa caataaatta tcaaatagaa    780
ggttgcaacc aaaacaactt ctaattttaa cttttcataa tagtggattc gagaggaatc    840
catgattttc ttggaaaata attttttagc acataatagc cctagcagag agaaccaaga    900
gagaaatttg gaaataagca aatactgata tatgaattag tgatttaatc ttaatttaat    960
taagcaatct tttatttaa cttccacgtc acttttcagg cgtgtattaa taagttagtt     1020
ccggacaaaa ttattttgt gcaacttagg taaaaattga atgattttg ggttacaaaa     1080
aaaaaaaaaa aaaaagaat agtgatcttt agtaacaaa tatgaaaatt gaatgaccat     1140
ccatgaaatt tactcttacc catgaaattt actcctataa gtactaacaa gaactttct     1200
tatttgtctg ttgttagatt aatcggtaga gcttcctata caatagttca accaaaata   1260
tctgatccgt cgttacaacc accaagcagt ttccttgact caaattaagt aaaggttaaa   1320
cctaattatt tctaggaaac tcttttcttg tctccatttg cccgtcttgt ccattaataa   1380
gaaaaacaaa tgaatttaag ttttatccac taatagtaaa aagaaaattc tacattacca   1440
atgttatatt ttggacaaat tctactaata ggttactgat cctcttatta ggattatcaa   1500
cttatagtca cctaaatgca gctagttta aacgatttgg ttgtgtaaat aattttaaa    1560
atacctcaaa attaaatcta tttttcttga aatcaaataa tttaagagg aaatctcaat    1620
tggtaatgct tcctttagta agttaattgt tgtaaatatt catgtgggat atatgaagtc   1680
aactctactt atattttagg taacgtaata atttaaaaaa tttaattaaa tagtaagtcc   1740
ctcgtctcac tttattttatc atacattttt tagtccatcc aaaaaagaat atcattttac   1800
cattaatgaa atgatttata ttcacacaga tacctattgt ttgttttaga tcataaattt   1860
taaaacactt ttttttattta ttaaattttg tgtcaagtca aaacatgaac gaatacagta   1920
tttaaaagtt aaactcaagc aaaaagaaaa agagatttgt aaagggctgt ttagagaata   1980
```

-continued

| | |
|---|---|
| tacagaagag atggaaataa atgcaaaggt cgcatgttac atgtccttcc cattcactca | 2040 |
| ctctgccttc atgcatacgc tttaattgag ctttttcttt tccctattaa ttaccttttg | 2100 |
| ccgttttaag taaaattact cctactgaat ccaaagtaca tctgatttaa caaatactaa | 2160 |
| taaatcagat ttgtcttaaa tatatttcta tttgtatata tctgttggtg gtggaatgct | 2220 |
| tgttacctac tcctttattc cactctctac ataacataag aactcccaag aaaacaaaaa | 2280 |
| cacacatact gagtgtgaaa atggagaaa cacaagtcat gtaagctatg ttttaggaag | 2340 |
| tttgctaatg gtagagcttt aggtgggcat atgagatctc acatgatgaa tctttatgta | 2400 |
| caaaaacaac aaatgactga tgaaatggag tattcaattc cttcatcttc atggtcctct | 2460 |
| ggtgaagtag ctgctggtga tgccgatgat tcgggtattg ttcttccaga taaggaaagt | 2520 |
| gaaactgagt catcaagaaa ccaagctcct tttagaaagt ccaaaggtc aagaaaatca | 2580 |
| agaattgtca agttaaaga gtactcatca ttggttgata cagagccagt aagttcaata | 2640 |
| tcagagaatt c | 2651 |

<210> SEQ ID NO 3
<211> LENGTH: 2991
<212> TYPE: DNA
<213> ORGANISM: Petunia hybrida

<400> SEQUENCE: 3

| | |
|---|---|
| gatatcgagc tagcccggcc cgattgacag gtataaccta gagtgtttca aatatgactc | 60 |
| gggattggag aaagtagtca gttatctgtt aatctttttt taagagttga aggtgggatg | 120 |
| tcaattttct taaactaaat gtagtgaaaa catattagtt acttcatttt acttactaat | 180 |
| gtaatgatta ctcccttcgg tccactttat ttgatttttt aatctttttt ttttgtccaa | 240 |
| ataattgat ttgttcaaaa ttcaaaaagt tattaaaggg ttcttcccaa atatactctt | 300 |
| attaataaat aatctaacac aatatttaaa agacctcaca gatttctaca aataaatttg | 360 |
| ataggaacaa aagttaatat cgtaaataat ctccttaatt aatgttaaaa ggtgaatttg | 420 |
| taaatatgtg tgaaaacaac aaaaaaaaat caagagtaac tatttgatcc caagaatatc | 480 |
| agtacttatt aggataaaga aagtaaaata atgtggaaat gaaatgaacg ctacgtataa | 540 |
| cacgttgtaa agggaacatg tcattattcc atacttttac caaacctaat gattggatga | 600 |
| aacataagat tgtaatggca gaaatataaa ttaggagaat tttcagaaag ccggcgtgat | 660 |
| ttttgggtcg taatcaatta actaagtaaa gtgatgaacc ttggttttag tagtagcaca | 720 |
| aaagtgggta gtgggtcaac tgcacatgga atttgcttca ttcattaaca tcactaactc | 780 |
| caatccaacc aagtccactc ccactagtta tgctcaacaa atatatttcc acactccatt | 840 |
| atcactccaa ctaatttttt gtttctccaa aaataacaaa cgatttctct tctaatgcat | 900 |
| agctagcatc attgtaatta gatatatcta agaaaatttt acatgacaaa cttgtgatct | 960 |
| tatcagcaat taagatttaa gtctcatcaa gctctttcat tttcctttt actacttcta | 1020 |
| ccgctgctac tccaaatgaa aaaacttgc ataaacactt tgataggta agcaaatcgc | 1080 |
| acctatgaac ttttttaaaa taatttaatg gtgttgttcg agctactatt ttgtacacat | 1140 |
| ctaaattatt ttatatgtac tatctcacag gtattgaata atttttgtcca ccaaaattta | 1200 |
| tcggtatatt gaaagaaatc atctaatgaa ttttaccttta atttgtttgg atcatttcac | 1260 |
| ttcattcagt gttaggcgac gtccttttag gctatagaat atacttatg gacttggcaa | 1320 |
| ttaaatttag tcattcttaa tgacaactga agctaaggta gttaattagt atttgatgat | 1380 |

```
atatttaaaa aatgcttcaa actgtgaagt aacttaaagg gtgtgaaatt aaagagagat   1440
ttatttttct tctgtatttt ttaattgaag gcgcaaattg tgtggtgcca ggcttgcact   1500
ccaatcctcc acaaggtatc gttggcataa agtaatgggg tttgcttcaa agccaaccga   1560
atcttactcc tttcctcacc tcctcatact tctcattact cattacattg catcttcccc   1620
ccccccccc cccccccacg tccccaaacc ataacctcta tatacatata catataatca   1680
ccttatatat ataactatat atatcattgc ctatatatat aacttgcaaa gtttgtaagt   1740
gcaagaaaac agtgaacatt ttcaagatca ctattcacgg gggcggcttc ttttcactt    1800
tacctaaaat ctccctttca ttcactacca ctcttccaaa acacatatat acactcactg   1860
tgttacatcg ttttctccat tcccttgtg aaataaaaca tacctttgcc tcttctttt    1920
gtttcttttt ccccacctct tgaaaaaggt cagtgacctt tgaattataa aaaagacaa    1980
aggcactaca atggaagttc aaatgcaaga agatcatgat catcacatga atatggtgat   2040
caaaagaagg agaactaaaa gaccaagacc atcttctcct ctagctttaa caattgctac   2100
tagctcatgt agcaccgtgg aagggactca tgctggtgaa ttggacggac atgtggcgaa   2160
ttcgtcgtct tcgccttcaa attctgggat tgatatactt atcagaaata gagaagaaga   2220
agatatggct aattgtttga ttcttttagc acaaggtcat aataaccaaa agccgtctcc   2280
ttctcattct ccattggatg tctaccaatg caaaacatgc aaccgttgtt tcccttcgtt   2340
tcaagcactt ggtggacata gagcaagtca taaaaaacca aaactaccaa ccaacttaga   2400
agagaaaaat tcaaagccaa ttgaacatgt tgagaattgt tccaagtcga acgaggatca   2460
tgtcacaact ttgtcacttc aaatttcgaa caataatatt aacaacaaca acagcaacaa   2520
caacaacaac aataacatca tcaagaataa gaataggggt catgaatgtt cgatttgtgg   2580
agcggaattt acttcagggc aagcattagg aggacacatg agacgacata gaccattacc   2640
aaatagtatt gcaattgcaa gtactagcca tgaattagag tcttctcatg aaataaagaa   2700
cacaaggaat ttcttgtcac tggaccttaa tctaccggcg cctgaagacg atcatcggcc   2760
agaaacgaaa ttctcatttg catcaaaaga acaagtcatc gtcttctcag cttctccttt   2820
ggttgattgc cattactaaa tcaacacact ggccctttat ttattttcg ctattttttt    2880
tttttttgta tttcttgatt tattttaatc atgacacaat tgtgaattat tgttaacacc   2940
ttattttat tattgtacat tcaacaattt attaatagac ataattcttt g             2991
```

<210> SEQ ID NO 4
<211> LENGTH: 31
<212> TYPE: DNA
<213> ORGANISM: Artificial Sequence
<220> FEATURE:
<223> OTHER INFORMATION: primer

<400> SEQUENCE: 4
ccggggatcc atcatcttgt agaagatcca t                              31

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
ccggggatcc acatgacttg tgtttctcca t                              31

<210> SEQ ID NO 6
<211> LENGTH: 31
<212> TYPE: DNA
<213> ORGANISM: Artificial Sequence
<220> FEATURE:
<223> OTHER INFORMATION: primer

<400> SEQUENCE: 6
ccggggatcc ttcttgcatt tgaacttcca t                            31

<210> SEQ ID NO 7
<211> LENGTH: 253
<212> TYPE: PRT
<213> ORGANISM: Petunia hybrida

<400> SEQUENCE: 7

Met Asp Leu Leu Gln Asp Arg Glu Ser Glu Thr Glu Ser Leu Pro Tyr
 1               5                  10                  15

Pro Thr Gln Cys Lys Arg Tyr Lys Arg Ile Ile Asn Ser Arg Ile Ser
            20                  25                  30

Asp Thr His Tyr Asn Gln Phe Leu Ser Leu Glu Arg Arg Arg Gln Gln
        35                  40                  45

Gln Gln Gln Gln Tyr Gly Lys Ile Thr Glu Phe Pro Phe Val Glu Ser
    50                  55                  60

Glu Pro Val Ser Ser Ile Ser Asp Thr Ser Pro Asp Glu Asp Val Ala
65                  70                  75                  80

Asn Cys Leu Met Met Leu Ser Arg Asp Lys Trp Met Thr Gln Glu Asn
                85                  90                  95

Glu Val Ile Asp Asn Ser Ala Ser Tyr Asp Glu Asp Val Lys Thr Glu
            100                 105                 110

Asp Ser Val Val Val Lys Val Thr Thr Thr Arg Arg Gly Arg Gly Lys
        115                 120                 125

Tyr Ile Cys Glu Thr Cys Asn Lys Val Phe Arg Ser Tyr Gln Ala Leu
    130                 135                 140

Gly Gly His Arg Ala Ser His Lys Lys Ile Lys Val Ser Ile Asn Glu
145                 150                 155                 160

Thr Lys Asn Asn Gly Asn Val Glu Ser Glu Val Gln Lys Asp Lys Ile
                165                 170                 175

His Glu Cys Pro Val Cys Tyr Arg Val Phe Ser Ser Gly Gln Ala Leu
            180                 185                 190

Gly Gly His Lys Arg Ser His Gly Ile Gly Val Ala Ala Thr Asn Val
        195                 200                 205

Ser Leu Ser Thr Lys Ile Val Ser Ser Arg Ile Ser Gly Thr Met Ile
    210                 215                 220

Asp Leu Asn Ile Pro Ala Thr Leu Glu Asp Glu Ile Ser Gln Ile
225                 230                 235                 240

Glu Val Ser Ala Val Ser Asp Asp Glu Phe Val Asn Pro
                245                 250

<210> SEQ ID NO 8
<211> LENGTH: 116
<212> TYPE: PRT
<213> ORGANISM: Petunia hybrida

<400> SEQUENCE: 8

Met Glu Lys His Lys Ser Cys Lys Leu Cys Phe Arg Lys Phe Ala Asn
 1               5                  10                  15

Gly Arg Ala Leu Gly Gly His Met Arg Ser His Met Met Asn Leu Tyr

```
                    20                  25                  30

Val Gln Lys Gln Gln Met Thr Asp Glu Met Glu Tyr Ser Ile Pro Ser
            35                  40                  45

Ser Ser Trp Ser Ser Gly Glu Val Ala Ala Gly Asp Ala Asp Asp Ser
        50                  55                  60

Gly Ile Val Leu Pro Asp Lys Glu Ser Glu Thr Glu Ser Ser Arg Asn
 65                 70                  75                  80

Gln Ala Pro Phe Arg Lys Ser Lys Arg Ser Arg Lys Ser Arg Ile Val
                85                  90                  95

Lys Val Lys Glu Tyr Ser Ser Leu Val Asp Thr Glu Pro Val Ser Ser
            100                 105                 110

Ile Ser Glu Asn
        115

<210> SEQ ID NO 9
<211> LENGTH: 282
<212> TYPE: PRT
<213> ORGANISM: Petunia hybrida

<400> SEQUENCE: 9

Met Glu Val Gln Met Gln Glu Asp His Asp His His Met Asn Met Val
 1               5                  10                  15

Ile Lys Arg Arg Arg Thr Lys Arg Pro Arg Pro Ser Ser Pro Leu Ala
            20                  25                  30

Leu Thr Ile Ala Thr Ser Ser Cys Ser Thr Val Glu Gly Thr His Ala
            35                  40                  45

Gly Glu Leu Asp Gly His Val Ala Asn Ser Ser Ser Ser Pro Ser Asn
        50                  55                  60

Ser Gly Ile Asp Ile Leu Ile Arg Asn Arg Glu Glu Asp Met Ala
 65                 70                  75                  80

Asn Cys Leu Ile Leu Leu Ala Gln Gly His Asn Asn Gln Lys Pro Ser
                85                  90                  95

Pro Ser His Ser Pro Leu Asp Val Tyr Gln Cys Lys Thr Cys Asn Arg
            100                 105                 110

Cys Phe Pro Ser Phe Gln Ala Leu Gly Gly His Arg Ala Ser His Lys
            115                 120                 125

Lys Pro Lys Leu Pro Thr Asn Leu Glu Glu Lys Asn Ser Lys Pro Ile
        130                 135                 140

Glu His Val Glu Asn Cys Ser Lys Ser Asn Glu Asp His Val Thr Thr
145                 150                 155                 160

Leu Ser Leu Gln Ile Ser Asn Asn Ile Asn Asn Asn Ser Asn
                165                 170                 175

Asn Asn Asn Asn Asn Ile Ile Lys Asn Lys Asn Arg Val His Glu
            180                 185                 190

Cys Ser Ile Cys Gly Ala Glu Phe Thr Ser Gly Gln Ala Leu Gly Gly
            195                 200                 205

His Met Arg Arg His Arg Pro Leu Pro Asn Ser Ile Ala Ile Ala Ser
        210                 215                 220

Thr Ser His Glu Leu Glu Ser Ser His Glu Ile Lys Asn Thr Arg Asn
225                 230                 235                 240

Phe Leu Ser Leu Asp Leu Asn Leu Pro Ala Pro Glu Asp Asp His Arg
                245                 250                 255

Pro Glu Thr Lys Phe Ser Phe Ala Ser Lys Glu Gln Val Ile Val Phe
            260                 265                 270
```

```
-continued

Ser Ala Ser Pro Leu Val Asp Cys His Tyr
    275                 280
```